US011045632B2

(12) United States Patent
Christopher et al.

(10) Patent No.: US 11,045,632 B2
(45) Date of Patent: Jun. 29, 2021

(54) CEREBRAL SPINAL FLUID SHUNT PLUG

(71) Applicant: Longeviti Neuro Solutions LLC, Hunt Valley, MD (US)

(72) Inventors: Jesse Christopher, Hunt Valley, MD (US); Bradley Rabinovitz, Annapolis, MD (US); Todd Johnson, Chalfont, PA (US)

(73) Assignee: LONGEVITI NEURO SOLUTIONS LLC, Hunt Valley, MD (US)

( * ) Notice: Subject to any disclaimer, the term of this patent is extended or adjusted under 35 U.S.C. 154(b) by 492 days.

(21) Appl. No.: 15/830,529

(22) Filed: Dec. 4, 2017

(65) Prior Publication Data

US 2018/0304055 A1    Oct. 25, 2018

Related U.S. Application Data

(60) Provisional application No. 62/488,966, filed on Apr. 25, 2017.

(51) Int. Cl.
*A61M 27/00* (2006.01)

(52) U.S. Cl.
CPC ... *A61M 27/006* (2013.01); *A61M 2205/0227* (2013.01); *A61M 2205/6054* (2013.01)

(58) Field of Classification Search
CPC .............. A61M 27/002; A61M 27/006; A61M 2205/0227; A61M 2205/6054
See application file for complete search history.

(56) References Cited

U.S. PATENT DOCUMENTS

| | | |
|---|---|---|
| 3,111,125 A | 11/1963 | Schulte |
| 3,310,051 A | 3/1967 | Schulte |
| 3,827,439 A | 8/1974 | Schulte et al. |
| 3,889,687 A | 6/1975 | Harris et al. |
| 4,206,762 A | 6/1980 | Cosman |
| 4,390,018 A | 6/1983 | Zukowski |
| 4,475,898 A | 10/1984 | Brodner et al. |
| 4,551,128 A | 11/1985 | Hakim et al. |
| 4,660,568 A | 4/1987 | Cosman |
| 4,781,673 A | 11/1988 | Watanabe |
| 4,885,002 A | 12/1989 | Watanabe et al. |
| 4,950,232 A | 8/1990 | Ruzicka et al. |
| 5,360,407 A * | 11/1994 | Leonard ............ A61M 39/0208 604/116 |
| 5,458,606 A | 10/1995 | Cohen et al. |
| 5,464,446 A | 11/1995 | Dreessen et al. |
| 5,643,195 A | 7/1997 | Drevet et al. |
| 5,928,182 A * | 7/1999 | Kraus ................ A61M 27/006 604/9 |
| 6,146,352 A | 11/2000 | Bonnal |
| 6,348,042 B1 | 2/2002 | Warren, Jr. |

(Continued)

FOREIGN PATENT DOCUMENTS

| | | |
|---|---|---|
| CA | 219104 | 5/1922 |
| CA | 2154700 | 6/1994 |

(Continued)

*Primary Examiner* — Tatyana Zalukaeva
*Assistant Examiner* — Heather K Barnwell
(74) *Attorney, Agent, or Firm* — Welsh Flaxman & Gitler LLC

(57) ABSTRACT

A cerebral spinal fluid shunt plug includes a shunt plug housing having a recess formed therein and a shunt valve shaped and dimensioned for positioning within the recess of the shunt plug housing.

15 Claims, 18 Drawing Sheets

(56) References Cited

U.S. PATENT DOCUMENTS

| | | |
|---|---|---|
| 6,383,159 B1 | 5/2002 | Saul et al. |
| 6,875,192 B1 | 4/2005 | Saul et al. |
| 7,235,060 B2 | 6/2007 | Kraus |
| 7,346,391 B1 | 3/2008 | Osorio et al. |
| 7,582,068 B2 | 9/2009 | Koullick et al. |
| 7,976,517 B2 | 7/2011 | Dextradeur et al. |
| 8,038,685 B2 | 10/2011 | Bedenbaugh |
| 8,202,090 B2 | 6/2012 | Shachar |
| 8,221,392 B2 | 7/2012 | Dextradeur et al. |
| 8,504,163 B1 | 8/2013 | Meadows |
| 8,940,799 B2 | 1/2015 | Bertrand et al. |
| 9,101,756 B1 | 8/2015 | Pianca et al. |
| 9,457,180 B2 | 10/2016 | Bucholz |
| 9,675,783 B2 | 6/2017 | Asaad et al. |
| 9,713,429 B2 | 7/2017 | Schmidt et al. |
| 9,861,799 B2 | 1/2018 | Trescony et al. |
| 2002/0169485 A1 | 11/2002 | Pless et al. |
| 2004/0010219 A1* | 1/2004 | McCusker .......... A61M 27/006 604/9 |
| 2004/0220510 A1 | 11/2004 | Koullick et al. |
| 2005/0059922 A1 | 3/2005 | Kuhlman et al. |
| 2008/0262406 A1 | 10/2008 | Wiener |
| 2009/0112277 A1 | 4/2009 | Wingeier et al. |
| 2009/0112308 A1* | 4/2009 | Kassem ................ A61M 39/22 623/1.24 |
| 2010/0076366 A1* | 3/2010 | Henderson, Sr. ... A61M 27/006 604/9 |
| 2013/0085441 A1* | 4/2013 | Aihara ................ A61M 27/002 604/9 |
| 2014/0073859 A1 | 3/2014 | Schorn |
| 2014/0074202 A1 | 3/2014 | Bedenbaugh |
| 2016/0220794 A1* | 8/2016 | Negre ................ A61M 27/006 |
| 2017/0361069 A1 | 12/2017 | Gazzani Romolo et al. |

FOREIGN PATENT DOCUMENTS

| | | |
|---|---|---|
| CA | 2382871 | 3/2001 |
| CA | 2462367 | 9/2004 |
| CA | 2516175 | 9/2004 |
| CN | 1370086 | 9/2002 |
| CN | 101715355 | 5/2010 |
| CN | 103598883 A | 2/2014 |
| DE | 2503990 | 8/1975 |
| DE | 69325384 | 1/2000 |
| DE | 602004019328 | 9/2004 |
| DE | 102004020856 | 4/2005 |
| DE | 602004015358 | 7/2008 |
| DE | 202012006700 | 8/2012 |
| DE | 202013002567 | 5/2013 |
| EP | 0135991 | 4/1985 |
| EP | 0798011 | 10/1997 |
| EP | 1207931 | 5/2002 |
| EP | 1248556 | 10/2002 |
| EP | 1596895 | 11/2005 |
| EP | 1649880 | 4/2006 |
| EP | 2019699 | 2/2009 |
| FR | 2695564 | 3/1994 |
| FR | 2698535 | 6/1994 |
| FR | 2746658 | 10/1997 |
| JP | H02193674 | 7/1990 |
| JP | 2003507140 | 2/2003 |
| JP | 4566595 | 10/2004 |
| JP | 5701469 | 4/2006 |
| JP | 2006517850 | 8/2006 |
| KR | 101012605 | 6/2005 |

* cited by examiner

CEREBRAL SPINAL FLUID SHUNT PLUG

CROSS REFERENCE TO RELATED APPLICATION

This application claims the benefit of U.S. Provisional Patent Application Ser. No. 62/488,966, entitled "CEREBRAL SPINAL FLUID SHUNT PLUG," filed Apr. 24, 2017.

BACKGROUND OF THE INVENTION

1. Field of the Invention

The present invention relates to a cerebral spinal fluid shunt plug.

2. Description of the Related Art

Hydrocephalus is a condition in which an excessive accumulation of cerebral spinal fluid is encountered. Cerebral spinal fluid is the clear fluid that surrounds the brain and the spinal cord. The excessive accumulation results in abnormal dilation of the ventricles within the brain. This dilation may cause the accumulation of potentially harmful pressure on the tissues of the brain.

Hydrocephalus is most often treated through the utilization of a shunt system. Cerebral spinal fluid shunt systems divert the flow of cerebral spinal fluid from a site within the ventricles to another area of the body where the cerebral spinal fluid can be absorbed as part of the circulatory system.

Shunt systems are commonly installed by creating a small hole within the skull, commonly referred to as a burr hole. A ventricular catheter is passed through the burr hole and positioned in the ventricular space. A peritoneal catheter is positioned at another location within the body where the cerebral spinal fluid can be diverted and absorbed. For example, it is common to either shunt the cerebral spinal fluid from the cerebral ventricles to the peritoneal cavity for reabsorption into the blood through the peritoneum or the cerebral spinal fluid may be shunted from the cerebral ventricles into the right atrium of the heart where the cerebral spinal fluid is directly shunted into the blood circulation.

In accordance with a typical procedure, incisions are made for the ventricular catheter and the peritoneal catheter. The peritoneal catheter is then positioned and a burr hole is formed within the skull. Thereafter, the ventricular catheter is positioned. The ventricular catheter and the peritoneal catheter are then connected to a shunt valve which controls the flow of cerebral spinal fluid from the ventricle, through the ventricular catheter, and to the peritoneal catheter. The incisions are then closed.

In addition to common complications, such as shunt malfunction, shunt failure and shunt infection, the utilization of catheters passing through the burr hole with the shunt valve positioned between the skull and the scalp results in other problems. For example, the shunt valve may resorb bone thereby creating a defect in the skull. In addition, the shunt valve and/or ventricular catheter are susceptible to movement. Still further, the ventricular catheter is susceptible to kinks as it passes through and around the burr hole.

With the foregoing in mind, it is desirable to improve upon current techniques for the placement of cerebral spinal fluid shunt systems.

SUMMARY OF THE INVENTION

It is, therefore, an object of the present invention to provide a cerebral spinal fluid shunt plug including a shunt plug housing having a recess formed therein and a shunt valve shaped and dimensioned for positioning within the recess of the shunt plug housing.

It is also an object of the present invention to provide a cerebral spinal fluid shunt plug wherein the shunt plug housing includes a bottom first housing member.

It is another object of the present invention to provide a cerebral spinal fluid shunt plug wherein the shunt plug housing includes top second housing member, the bottom first housing member and top second housing member being shaped and dimensioned for mating so as to define the shunt plug housing in which the shunt valve is positioned.

It is a further object of the present invention to provide a cerebral spinal fluid shunt plug wherein the recess is defined by recessed surfaces formed along the surfaces of the first housing member and the second housing member.

It is also an object of the present invention to provide a cerebral spinal fluid shunt plug wherein the shunt plug housing includes access holes or passageways allowing the recess to communicate with an exterior of the shunt plug housing, the access holes or passageways being shaped and dimensioned to allow for connection of a ventricular catheter and a peritoneal catheter with the shunt valve housed within the recess of the shunt plug housing.

It is another object of the present invention to provide a cerebral spinal fluid shunt plug wherein the shunt plug housing has a surface area along its upper surface of at least five $cm^2$ so as to accommodate various shunt valves and to provide the necessary space for placement of the shunt valve within the recess defined within the shunt plug housing.

It is a further object of the present invention to provide a cerebral spinal fluid shunt plug including bumps used in identifying a specific point or points on the cerebral spinal fluid shunt plug.

It is also an object of the present invention to provide a cerebral spinal fluid shunt plug including magnets or ferromagnetic properties used in identifying a specific point or points on the cerebral spinal fluid shunt plug.

It is another object of the present invention to provide a cerebral spinal fluid shunt plug including an RFID (radio-frequency identification) device used in identifying a specific point or points on the cerebral spinal fluid shunt plug.

It is a further object of the present invention to provide a cerebral spinal fluid shunt plug including radiographic and/or acoustic properties used in identifying a specific point or points on the cerebral spinal fluid shunt plug.

It is also an object of the present invention to provide a method for installation of a shunt valve. The method includes the steps of making an incision and creating a cranial hole, positioning a ventricular catheter and a peritoneal catheter, and connecting the ventricular catheter and the peritoneal catheter to a shunt valve forming part of cerebral spinal fluid shunt plug. The cerebral spinal fluid shunt plug includes a shunt plug housing including a recess formed therein and the shunt valve shaped and dimensioned for positioning within the recess of the shunt plug housing. The method further includes positioning and securing the cerebral spinal fluid shunt plug within the cranial hole.

It is also an object of the present invention to provide a method for installation of a shunt valve wherein the cerebral spinal fluid shunt plug is mounted within the cranial hole such that an upper surface of the cerebral spinal fluid shunt plug is substantially flush with an outer surface of the skull.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
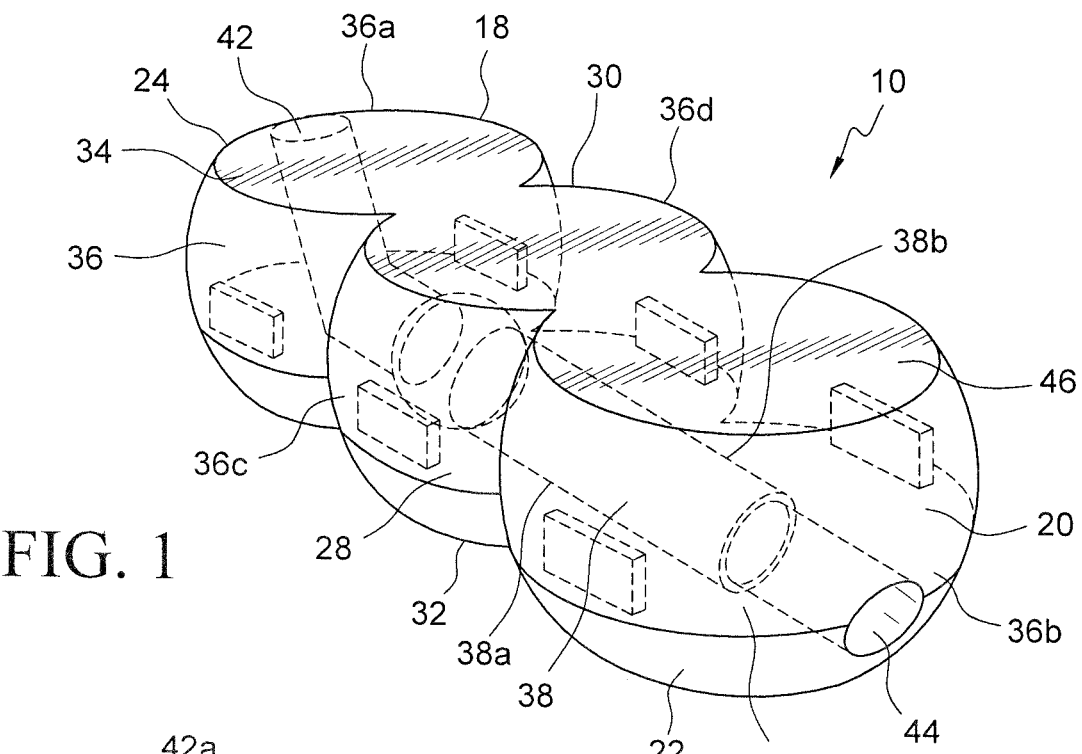
FIG. 1 is a perspective view of a shunt plug housing for a shunt plug in accordance with the present invention.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 7, various embodiments of a cerebral spinal fluid shunt plug 10 are disclosed in accordance with the present invention. It should be appreciated similar reference numerals are used for the various different embodiments. The shunt plug 10 is shaped and dimensioned for positioning within a physician formed cranial hole 100. The shunt plug 10 is further shaped and dimensioned for housing a shunt valve 12 in a reliable and secure manner so that a ventricular catheter 14 and peritoneal catheter 16 may be positioned without fear that the shunt valve 12 might move and/or the catheters 14, 16 might become disengaged from their desired locations.

The shunt plug 10 includes a shunt plug housing 18 composed of a bottom first housing member 20 and a top second housing member 22. The bottom first housing member 20 and top second housing member 22 are shaped and dimensioned for mating so as to define the shunt plug housing 18 in which the shunt valve 12 is positioned. In accordance with the disclosed embodiments, the shunt valve 12 will be placed within the shunt plug housing 18, so as to create the shunt plug 10 of the present invention, at the time of surgery.

Figure 3:
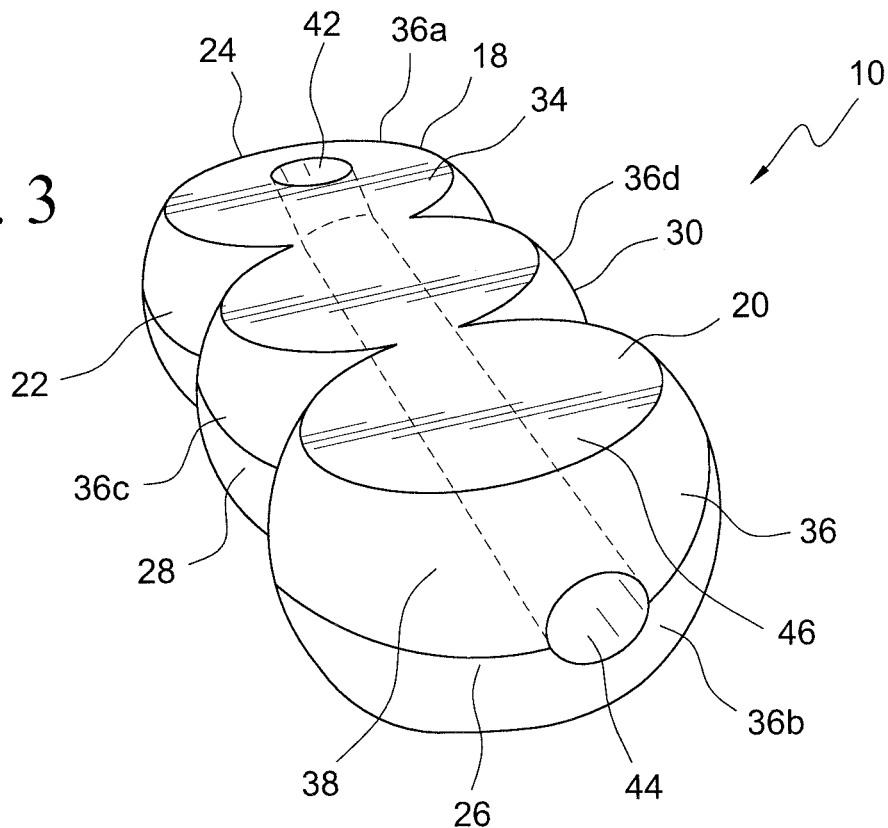
FIG. 3 is a perspective view of the shunt plug housing of the present invention with alternate positions for the access apertures.

The shunt plug housing 18, when the first housing member 20 and the second housing member 22 are connected together as shown with reference to FIGS. 1 and 3, includes a first end 24, a second end 26, a first lateral side 28, and a second lateral side 30. The shunt plug housing 18 also includes an upper surface 32, a lower surface 34, and a continuous side wall 36 extending between the upper surface 32 and the lower surface 34, as well as about the periphery of the shunt plug housing 18.

In accordance with the disclosed embodiments, and considering the procedure discussed below in greater detail, the shunt plug housing 18 is structured with consecutive and overlapping cylinders (for example, three cylinders as shown with reference to FIGS. 1, 2, and 3 and six cylinders as disclosed with reference to FIGS. 4, 5, and 6). While a shape in accordance with the disclosed embodiment is disclosed herein for the purpose of explaining the present invention, it is appreciated various shapes may be employed within the spirit of the present invention. As will be appreciated after reading the installation procedure presented below, the consecutive and overlapping cylinder structure was selected as a means of optimizing the installation procedure based upon the utilization of a single trephine to create consecutive and overlapping burr holes that ultimately define the cranial hole 100 in which the shunt plug 10 is positioned. As such, the shape of the shunt plug and the mechanism for the creation of the cranial hole are intimately related and may be varied based upon various needs and requirements.

Figure 2:
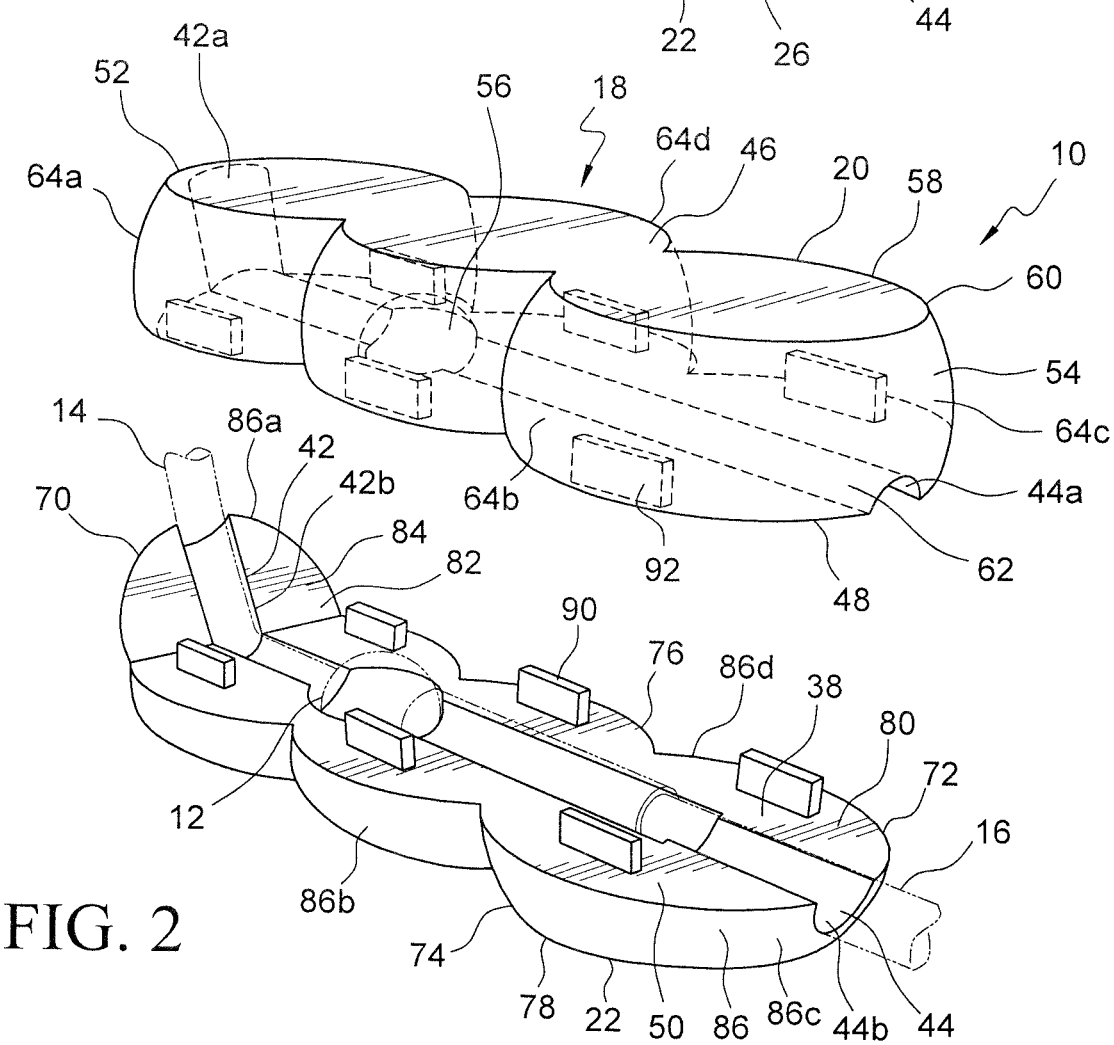
FIG. 2 is an exploded view of the shunt plug housing shown in FIG. 1.

Considering the embodiment disclosed with reference to FIGS. 1, 2, and 3, the side wall 36 of the disclosed embodiment is formed with a scalloped shape wherein a plurality of arcuate segments extends about the periphery of the shunt plug housing 18. The arcuate segments 36a, 36b at the first end 24 and the second end 26 of the shunt plug housing 18 define and an arcuate surface of approximately 220 degrees to 320 degrees, and the arcuate segments 36c, 36d located at the center of the side wall 36 along the first and second lateral sides 28, 30 define an arc of approximately 40 to 140 degrees. In accordance with a preferred embodiment, the outer surface of the side wall 36 may be bowed outwardly so as to define a convex outer surface.

Figure 4:
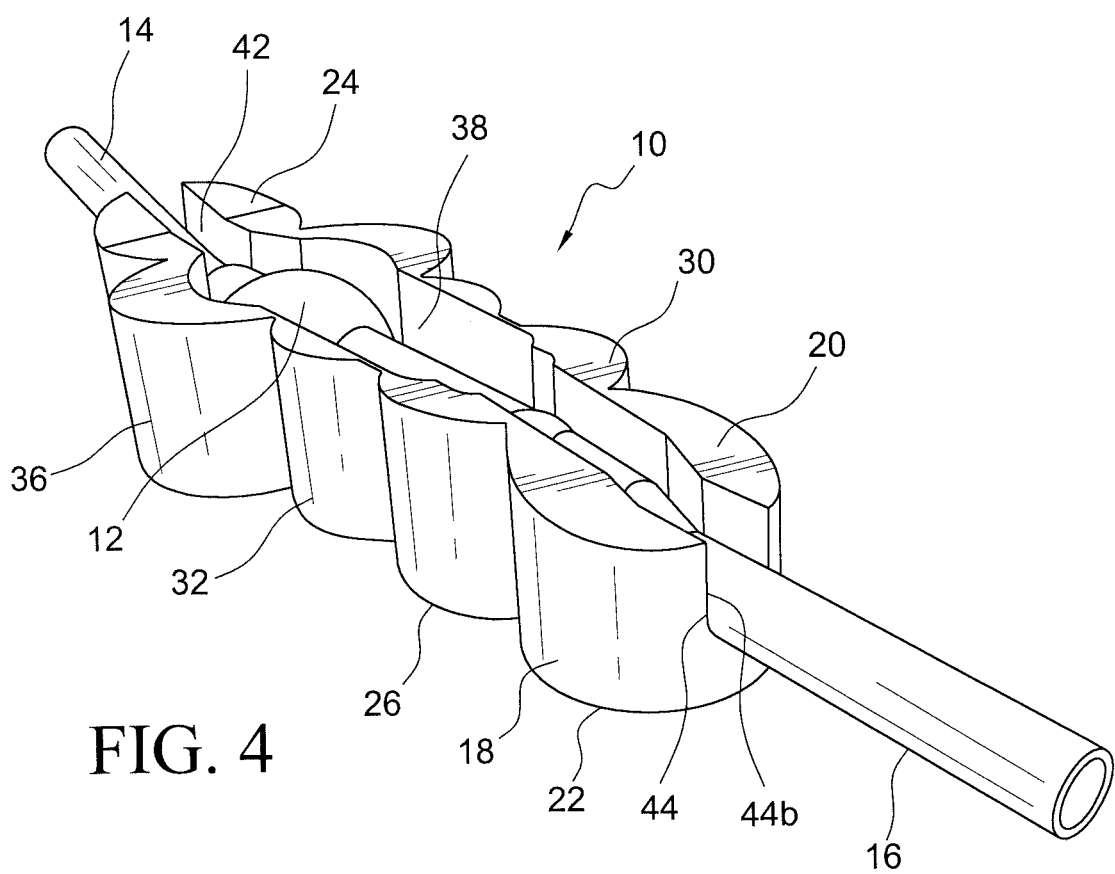
FIGS. 4, 5, and 6 are sectional views of the shunt plug, including the shunt plug housing, the shunt valve, and the catheters, wherein the top portion of the shunt plug housing has been cut away to more clearly show the shunt valve.
Figure 5:
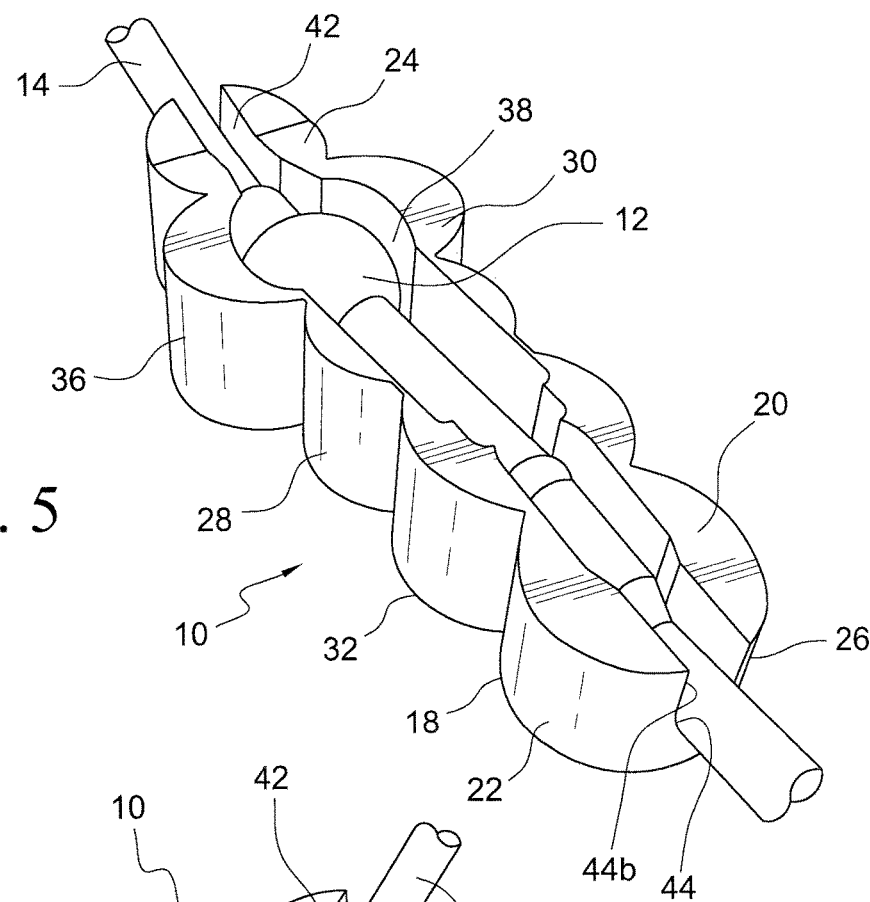
Figure 6:
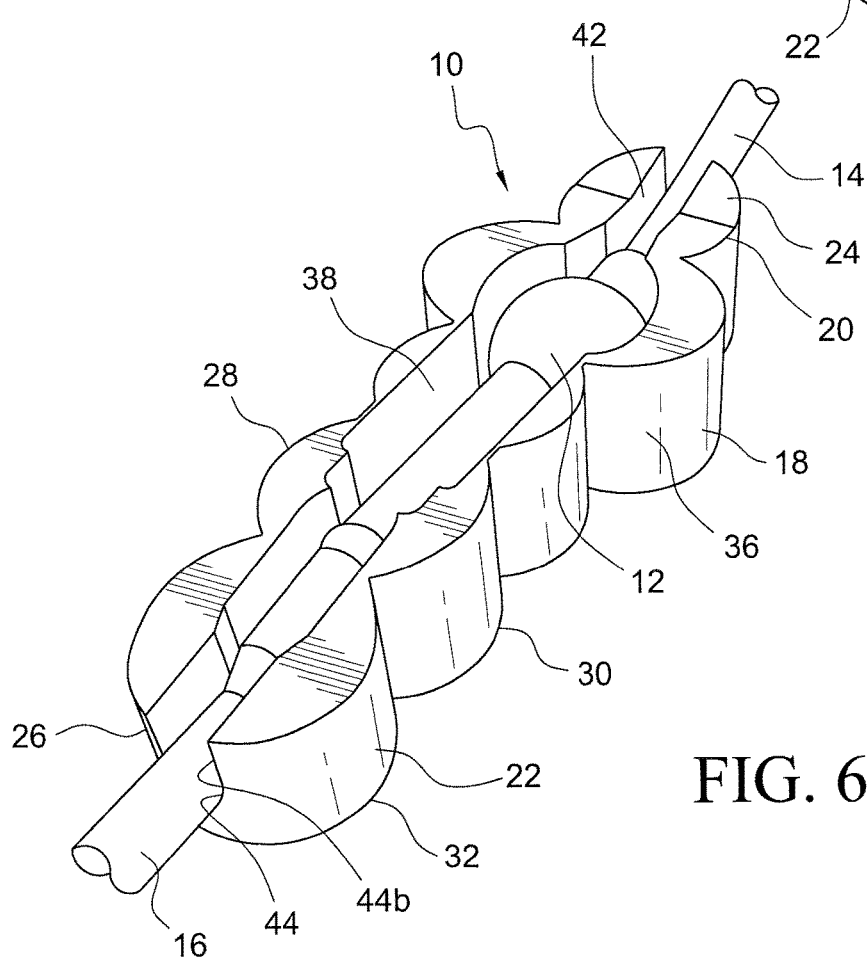

The embodiment disclosed with reference to FIGS. 4, 5, and 6 is similarly shaped, but includes additional arcuate surfaces requiring the formation of additional burr holes during the installation process. In particular, the shunt plug 10 disclosed in FIGS. 4, 5, and 6 would require the formation of six burr holes in a highly specific pattern. The pattern employed creates a larger area for accommodating the needs of shunt valves having larger dimensions.

A recess 38 is formed within the shunt plug housing 18. The recess 38 is defined by recessed surfaces 38a, 38b formed along the surfaces of the first housing member 20 and the second housing member 22. The recess 38 is in communication with the exterior of the shunt plug housing 18 via access holes 42, 44 extending from the exterior surface of the shunt plug housing 18 to the recess 38. As will be explained below in greater detail, these access holes 42, 44 allow for connection of the ventricular catheter 14 and the peritoneal catheter 16 with the shunt valve 12 housed within the recess 38 of the shunt plug housing 18. As with the recess 38, the access holes 42, 44 are defined by recessed surfaces 42a, 42b, 44a, 44b formed along the surfaces of the first housing member 20 and the second housing member 22. Depending upon the shape of the shunt plug housing 18 and the shunt valve 12 to be positioned therein, the position of the access holes 42, 44 may be varied to optimize the ultimate positioning of the peritoneal catheter 16 and the ventricular catheter 14 (see, for example, FIGS. 1 and 3).

In particular, and with reference to FIG. 2, the first housing member 20 includes an exterior surface 46 that defines the exterior surface of the shunt plug housing 18 when the first and second housing members 20, 22 are connected together (as shown in FIG. 1) to form the complete shunt plug housing 18. The first housing member 20 also includes a mating surface 48 that engages the mating surface 50 of the second housing member 22 when the first and second housing members 20, 22 are connected together to form the complete shunt plug housing 18.

With this in mind, the first housing member 20 includes a first end 52, a second end 54, and first and second lateral sides 56, 58. The first housing member 20 also includes a top surface 60 defining the lower surface 34 of the shunt plug housing 18, a lower surface 62 that forms part of the mating surface 48 of the first housing member 20 that mates with the mating surface 50 of the second housing member 22 so as to define the junction of the first housing member 20 and the second housing member 22, as well as the recess 38 in which the shunt valve 12 is positioned. The first housing member 20 also includes side walls 64a-d extending between the top surface 60 and the lower surface 62. The side walls 64b, 64c, 64d at the first and second lateral sides 56, 58, as well as the second end 54, of the first housing member 20 define a portion of the exterior surface of the shunt plug housing 18. The side wall 64a at the first end 52 of the first housing member 20 forms part of the mating surface 48 of the first housing member 20 that mates with the mating surface 50 of the second housing member 22 so as to define the junction of the first housing member 20 and the second housing member 22.

The second housing member 22 includes a first end 70, a second end 72, and first and second lateral sides 74, 76. The second housing member 22 includes a top surface 78 defining the upper surface 32 of the shunt plug housing 18, a lower surface 80 that forms part of the mating surface 50 of the second housing member 22 that mates with the mating surface 48 of the first housing member 20 so as to define the junction of the first housing member 20 and the second housing member 22, as well as the recess 38 in which the shunt valve 12 is positioned. The second housing member 22 also includes an upwardly directed wall portion 82 extending upwardly from the lower surface 80 at the first end 70 of the second housing member 22. The wall portion 82 includes an interior surface 84 forming part of the mating surface 50 of the second housing member 22 that mates with the mating surface 48 of the first housing member 22 so as to define the junction of the first housing member 20 and the second housing member 22. In particular, the interior surface 84 of the wall portion 82 is shaped and dimensioned to mate with the side wall 64a at the first end 52 of the first housing member 20. The surface of the wall portion 82 opposite the interior surface 84 forms part of the side wall of the shunt plug housing 18 at the first end 24 of the shunt plug housing 18.

The second housing member 22 also includes side walls 86a-d extending between the lower surface 80 and the top surface 78. The side walls 86a-d at the first and second lateral sides 74, 76, as well as the first and second ends 70, 72, of the second housing member 22 define a portion of the exterior surface of the shunt plug housing 18.

Mating of the first housing member 20 with the second housing member 22 is further facilitated by the provision of protrusions 90 along the lower surface 80 of the second housing member 22 and matingly shaped indentations 92 along the lower surface 62 of the first housing member 20.

As discussed above, the recess 38 in which the shunt valve 12 is positioned, as well as the access holes 42, 44 for the passage of the ventricular and peritoneal catheters 14, 16, is formed within the shunt plug housing 18. The recess 38 and access holes 42, 44 are defined by recessed surfaces 38a, 38b, 42a, 42b, 44a, 44b formed along the surfaces of the first housing member 20 and the second housing member 22. In particular, the recessed surfaces 38a, 38b, 42a, 42b defining the recess 38 and the first access hole 42 are formed along the lower surface 80 of the second housing member 22 and the lower surface 62 of the first housing member 20. The recessed surfaces 44a, 44b defining the second access hole 44 are formed along the side wall 64a of the first housing member 20 at the first end 52 thereof and along the interior surface 84 of the wall portion 82 at the first end 70 of the second housing member 22.

With the foregoing description of the first housing member and the second housing member in mind, it is appreciated that the first and second housing members may take various shapes depending upon the desired inter-engagement of these two members when the shunt plug housing is fully formed and ready for use.

As briefly discussed above, the recess 38 defined within the shunt plug housing 18 is shaped and dimensioned for placement of the shunt valve 12 therein. As those skilled in the art will appreciate, a variety of shunt valves are known in the art and the present shunt plug housing 18 may be adapted to accommodate a variety of these shunt valves. For example, the following shunt valves may be used in conjunction with the present invention: CODMAN®/Integra HAKIM® and Certas Programmable Shunt Valve, MEDTRONIC® STRATA®, SOPHYSA® POLARIS®, Ascuelap proGAV®, and INTEGRA® OSV II®. The present invention may also be used in conjunction with the Rickam reservoir and other similar reservoirs used in cerebral spinal fluid management. In accordance with a preferred embodiment, the shunt plug housing 18 should have a surface area along its upper surface 32 of at least five $cm^2$ so as to accommodate various shunt valves and to provide the necessary space for placement of the shunt valve 12 within the recess 38 defined within the shunt plug housing 18.

Once the shunt valve 12 is positioned between the first housing member 20 and the second housing member 22 within the recess 38 defined thereby, the first housing member 20 may be connected to the second housing member 22 so as to fully enclose the shunt valve 12 therein. Thereafter, the shunt plug 10 of the present invention may be utilized for the purpose of performing a cerebral spinal fluid shunt procedure.

In accordance with yet another embodiment of the present invention as shown with reference to FIGS. 9 to 18 (which shows this embodiment in various shapes to accommodate shunt valves from various manufacturers), the shunt plug is structured such that the shunt valve is uncovered. In particular, and as with the previous embodiment, the shunt plug 210 is shaped and dimensioned for housing a shunt valve 212 in a reliable and secure manner so that a ventricular catheter 214 and peritoneal catheter 216 may be positioned without fear that the shunt valve 212 might move and/or the catheters 214, 216 might become disengaged from their desired locations.

The shunt plug 210 includes a shunt plug housing 218 composed of a bottom first housing member 220. In accordance with the disclosed embodiments, the shunt valve 212 will be placed within the shunt plug housing 218, so as to create the shunt plug 210 of the present invention, at the time of surgery.

Figure 15:
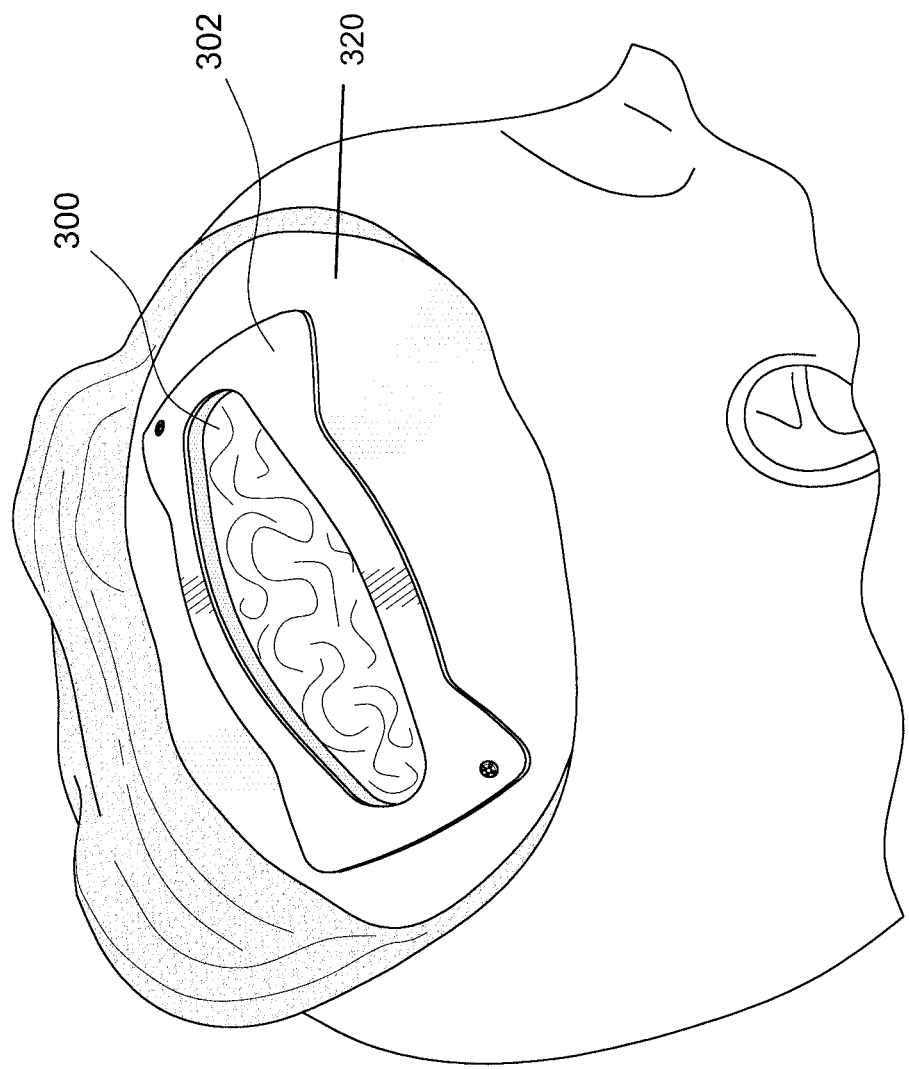
Figure 16:
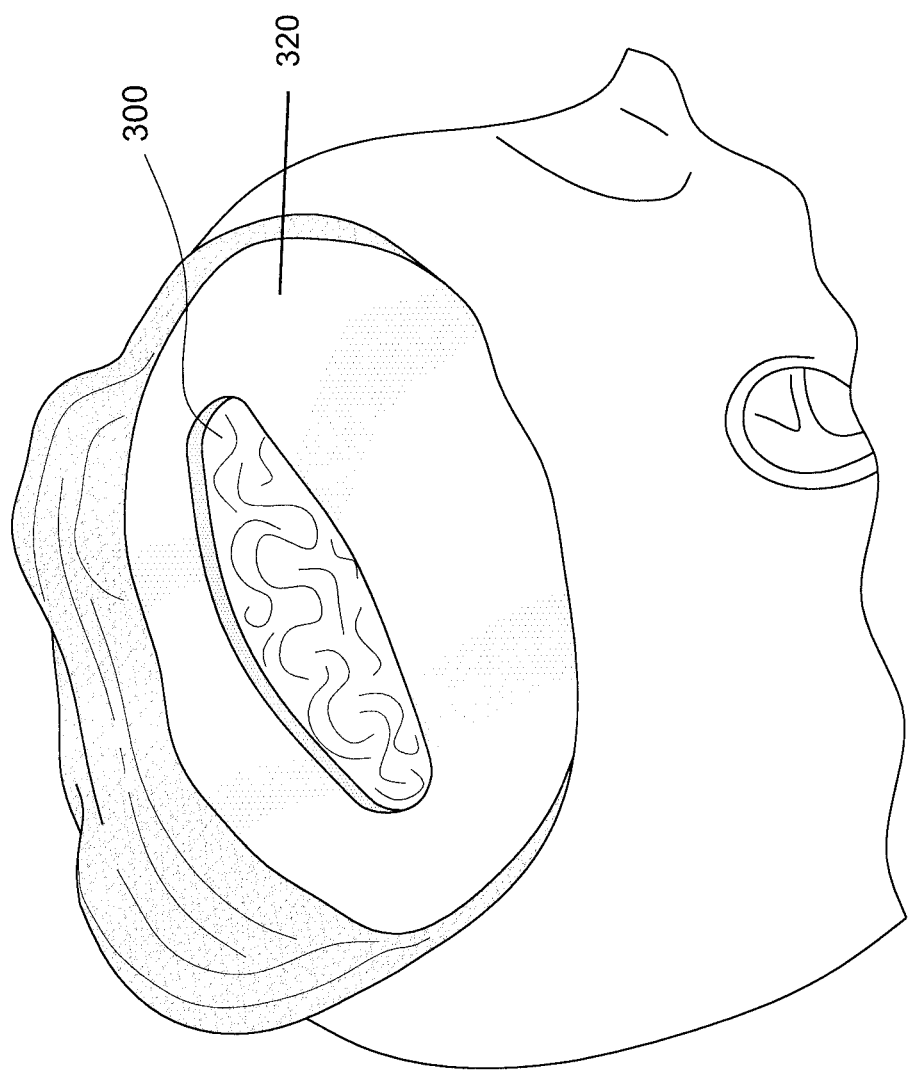
Figure 17:
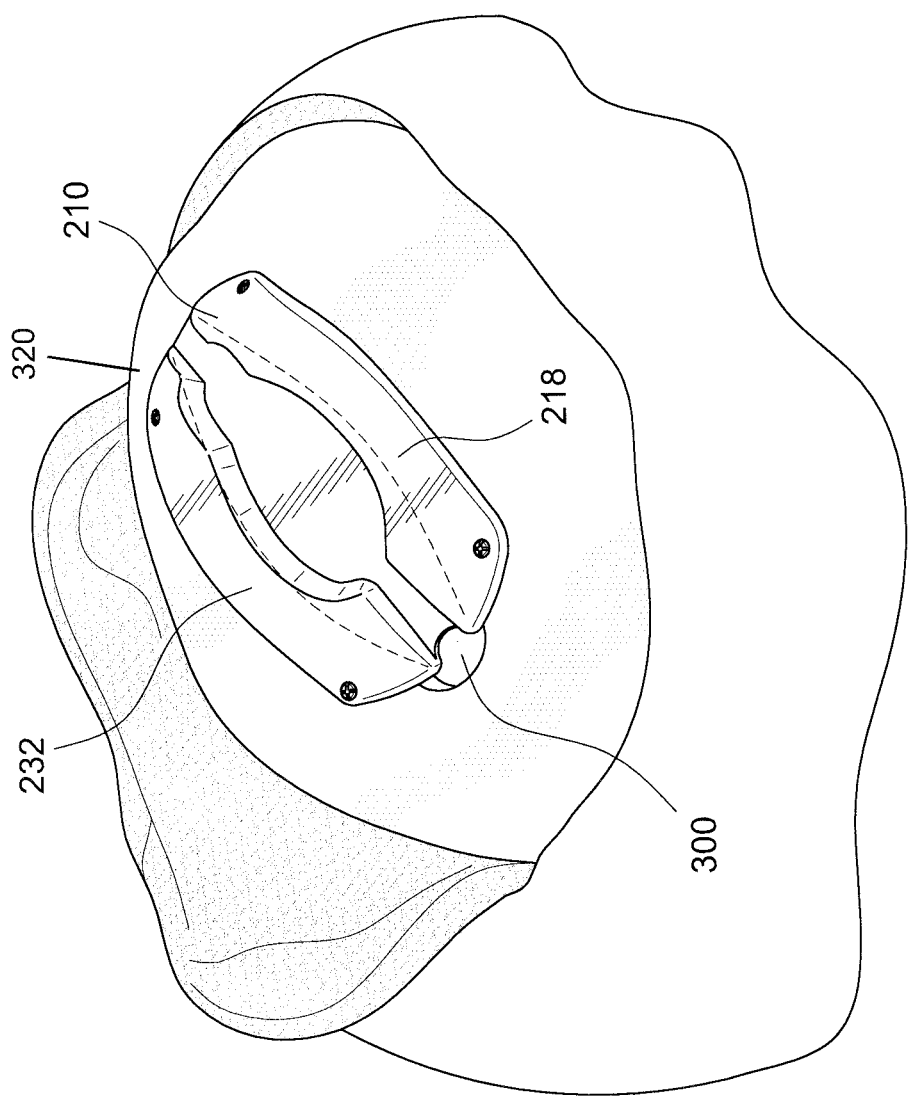
Figure 18:
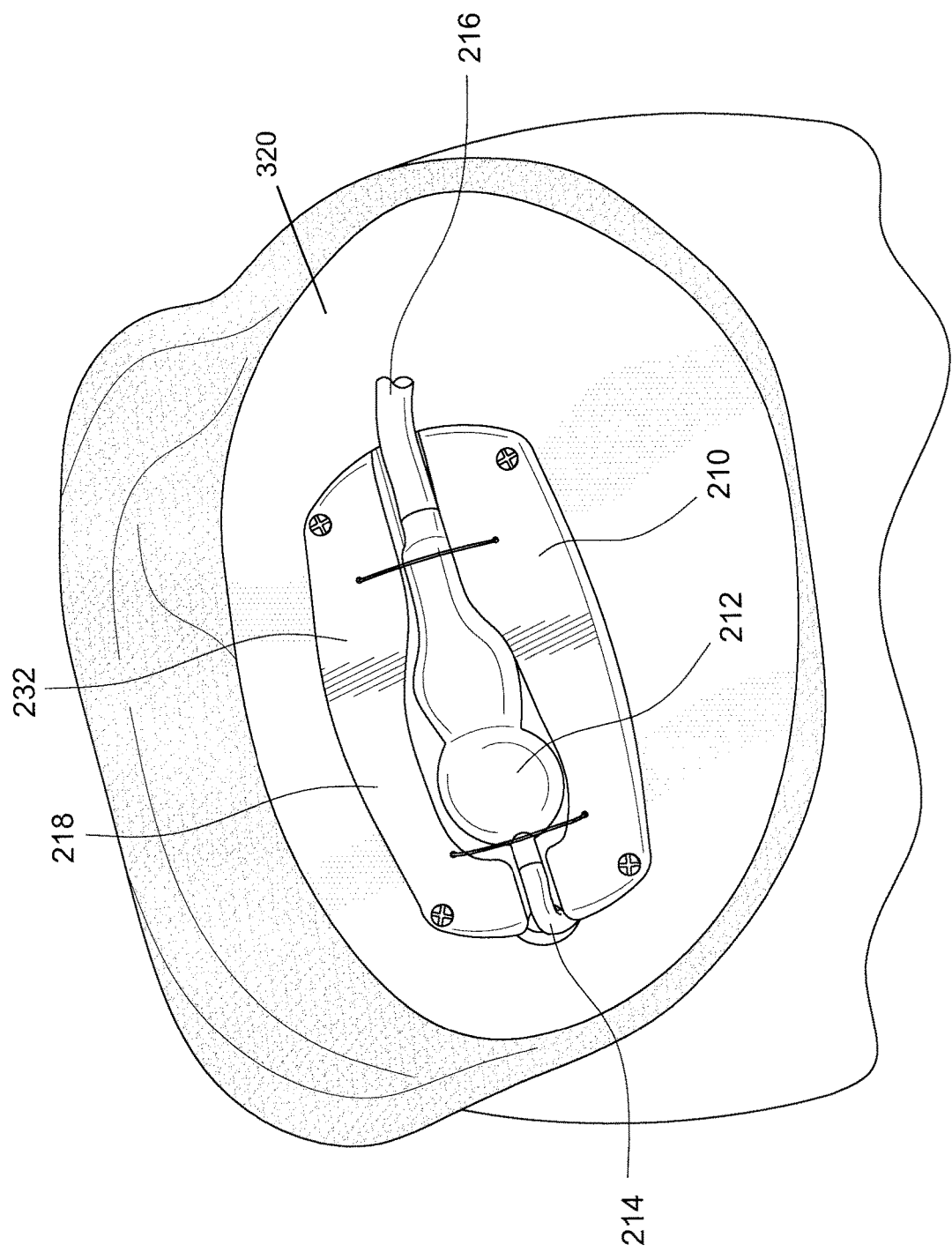

The shunt plug housing 218 includes a first end 224, a second end 226, a first lateral side 228, and a second lateral side 230. The shunt plug housing 218 also includes an upper surface 232, a lower surface 234, and continuous side walls 236a-d extending between the upper surface 232 and the lower surface 234, as well as about the periphery of the shunt plug housing 218. As will be appreciated based upon the following disclosure, the lower surface 234 is provided with a projection 234p that ultimately fits within the cranial hole 300 to assist in holding the shunt plug 210 in position after installation. With this in mind, the projection 234p is elliptically shaped to fit within the cranial hole 300 as shown in FIG. 15.

While particular shapes of the shunt plug housing 218 in accordance with the disclosed embodiment are disclosed herein for the purpose of explaining the present invention, it is appreciated various shapes may be employed within the spirit of the present invention. As such, the shape of the shunt plug and the mechanism for the creation of the cranial hole are intimately related and may be varied based upon various needs and requirements. For example, and in contrast with the embodiments described above with reference to FIGS. 1 to 6, the shunt plug housing includes a substantially elliptical shape.

A recess 238 is formed within the upper surface 232 of the shunt plug housing 218. The recess 238 is in communication with the exterior of the shunt plug housing 218 via access passageways 242, 244 extending from the exterior surface of the shunt plug housing 218 to the recess 238. As will be explained below in greater detail, these access holes (or passageways) 242, 244 allow for connection of the ventricular catheter 214 and the peritoneal catheter 216 with the shunt valve 212 housed within the recess 238 of the shunt plug housing 218. The access passageways 242, 244 are defined by recessed surfaces formed along the upper surface 232 of the shunt plug housing 218. Depending up the shape of the shunt plug housing 218 and the shunt valve 212 to be positioned therein, the position of the access holes (or passageways) 242, 244 may be varied to optimize the ultimate positioning of the peritoneal catheter 216 and the ventricular catheter 214.

As discussed above, the recess 238 in which the shunt valve 212 is positioned, as well as the access holes 242, 244 for the passage of the ventricular and peritoneal catheters 214, 216, is formed within the shunt plug housing 218. The recess 238 and access holes 242, 244 are defined by recessed surfaces 238a, 242a, 244a formed along the upper surface 232 of the shunt plug housing 218. In particular, the recessed surface 238a defining the recess 238 is formed along the upper surface 232 of the shunt plug housing 218; the recessed surface 242a defining the first access hole (or passageway) 242 is formed along the upper surface 232 adjacent the first end 224; and the recessed surfaces 244a defining the second access hole (or passageway) 244 are formed along the side wall 264a of the shunt plug housing 218 at the second end 226 thereof.

As briefly discussed above, the recess 238 defined within the shunt plug housing 218 is shaped and dimensioned for placement of the shunt valve 212 therein. As those skilled in the art will appreciate, and as explained above in conjunction with the prior embodiment, a variety of shunt valves are known in the art and the present shunt plug housing 218 may be adapted to accommodate a variety of these shunt valves. The present invention may also be used in conjunction with the Rickam reservoir and other similar reservoirs used in cerebral spinal fluid management. In accordance with a preferred embodiment, the shunt plug housing 218 should have a surface area along its upper surface 232 of at least five $cm^2$ so as to accommodate various shunt valves and to provide the necessary space for placement of the shunt valve 212 within the recess 238 defined within the shunt plug housing 218.

Once the shunt valve 212 is positioned within the recess 238 of the shunt plug housing 218 the shunt plug 210 of the present invention may be utilized for the purpose of performing a cerebral spinal fluid shunt procedure.

Figure 7:
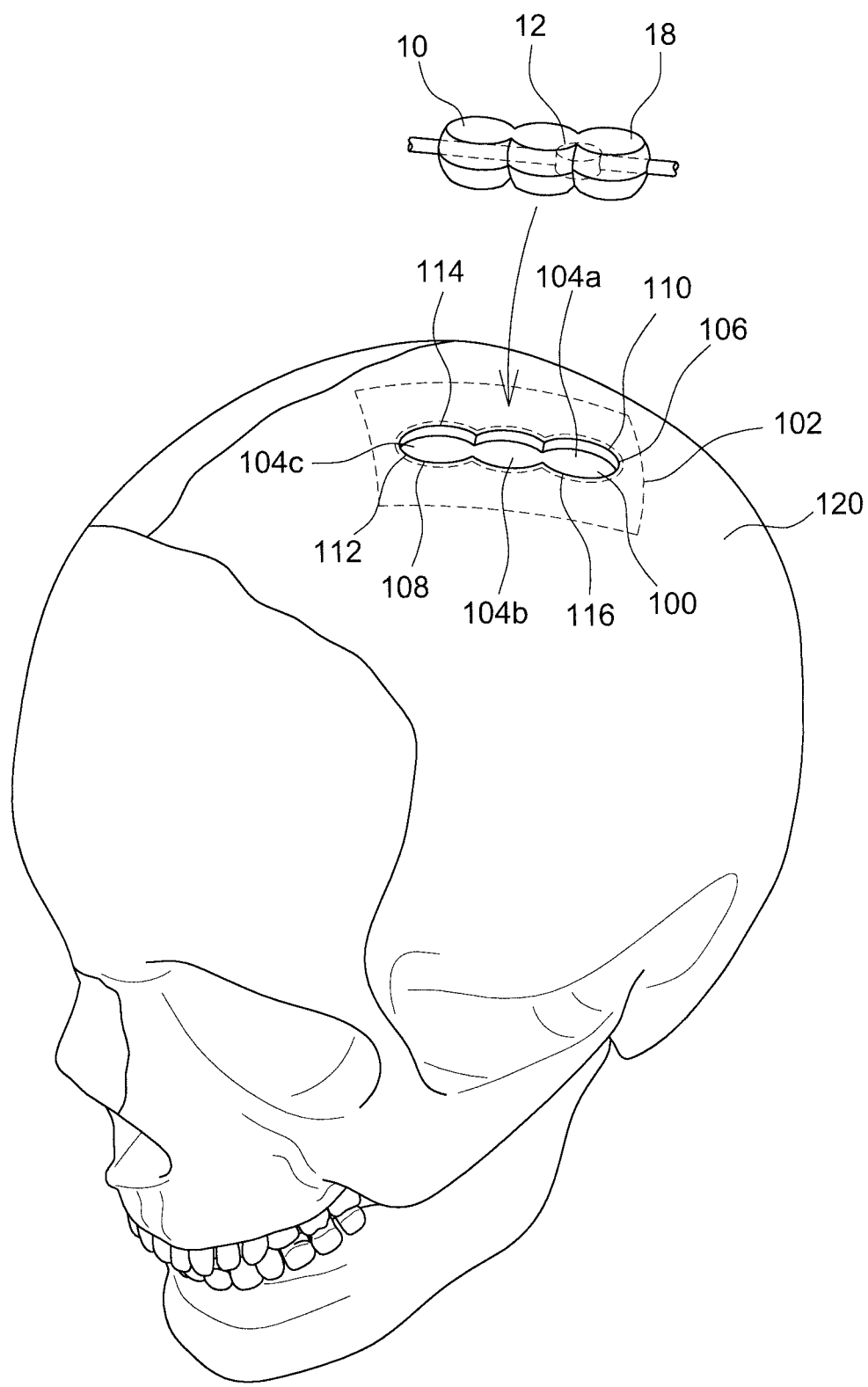
FIG. 7 is an exploded representative view of the installation process.

Referring to FIG. 7, and with particular reference to the embodiment disclosed in FIGS. 1, 2, and 3, the procedure is first initiated by making the required incision for passage of the peritoneal catheter 16. Thereafter, a cranial incision is made and the cranial hole 100 is created utilizing a template 102 (shown in broken lines) and predefined trephine (not shown). In contrast to prior art procedures, a singular burr hole is not formed. Rather, adjacent circular holes 104a-c (for example, three as shown in the disclosed embodiment) are formed creating the cranial hole 100 that is shaped for snuggly fitting the shunt plug 10 therein. As with the shape of the shunt plug 10, the cranial hole 100 created in accordance with the present invention includes scalloped edges. In particular, the cranial hole 100 includes first and second ends 106, 108 with an arcuate surface 110, 112 of approximately 220 to 320 degrees, as well as first and second lateral arcuate surfaces 114, 116 of approximately 40 to 140 degrees. Given the matching shape of the cranial hole 100 and the shunt plug 10, the shunt plug 10 will fit snugly within the cranial hole 100 thereby minimizing potential movement after completion of the procedure.

With the cranial hole 100 completed, the ventricular catheter 14 is positioned within the ventricle and the peritoneal catheter 16 is positioned with the body as using well know medical procedures. Thereafter, the ends of the peritoneal catheter 16 and the ventricular catheter 14 adjacent the shunt plug 10 may be secured to the shunt valve 12 housed within the shunt plug 10 by passing the ends of the respective catheters into the first and second access holes 42, 44 formed at locations along the exterior of the shunt plug housing 18. Thereafter, the shunt plug 10 is positioned within the cranial hole 100. The shunt plug 10 is mounted within the cranial hole 100 such that the upper surface 32 is substantially flush with the outer surface of the skull 120. It is, however, appreciated the exact positioning of the shunt plug will vary based upon specific anatomical characteristics of the patient. Once the shunt plug 10 is properly positioned, the shunt valve 12 is actuated utilizing well known procedures, and the procedure is completed in accordance with known medical procedures.

Figure 8:
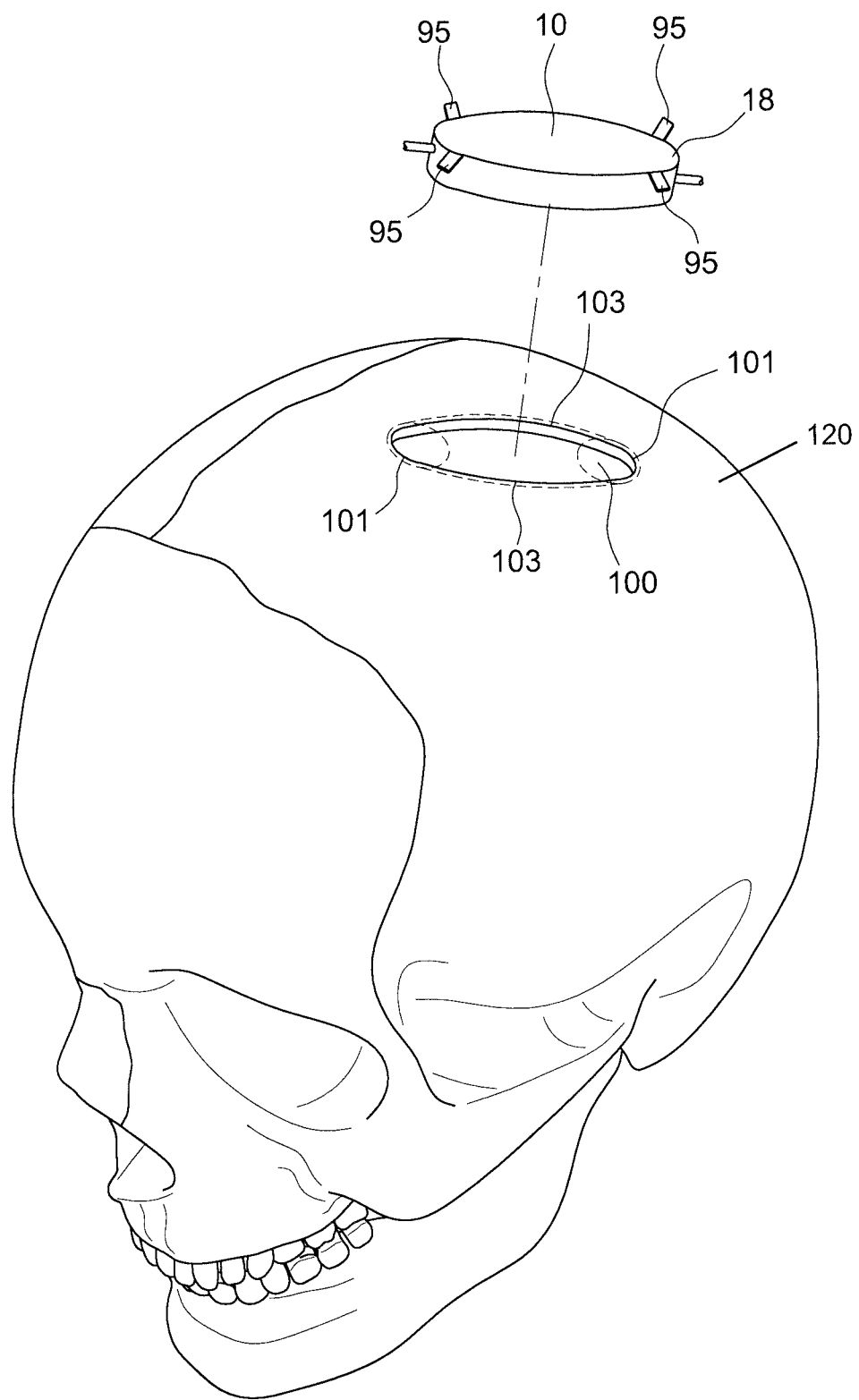
FIG. 8 is an exploded representative view of the installation process with a shunt plug of an alternate shape.
Figure 9:
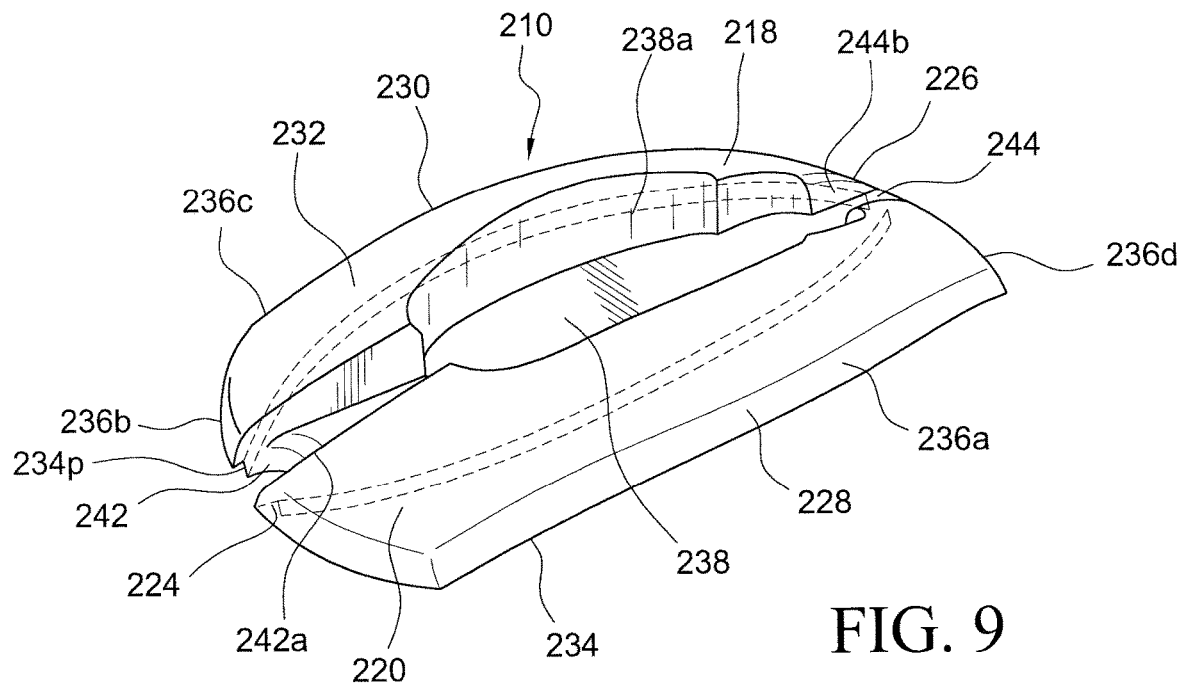
FIGS. 9, 10, and 11 are perspective views of a shunt plug housing in accordance with an alternate embodiment, and showing three different cavity shapes for accommodating different shunt valves.
Figure 10:
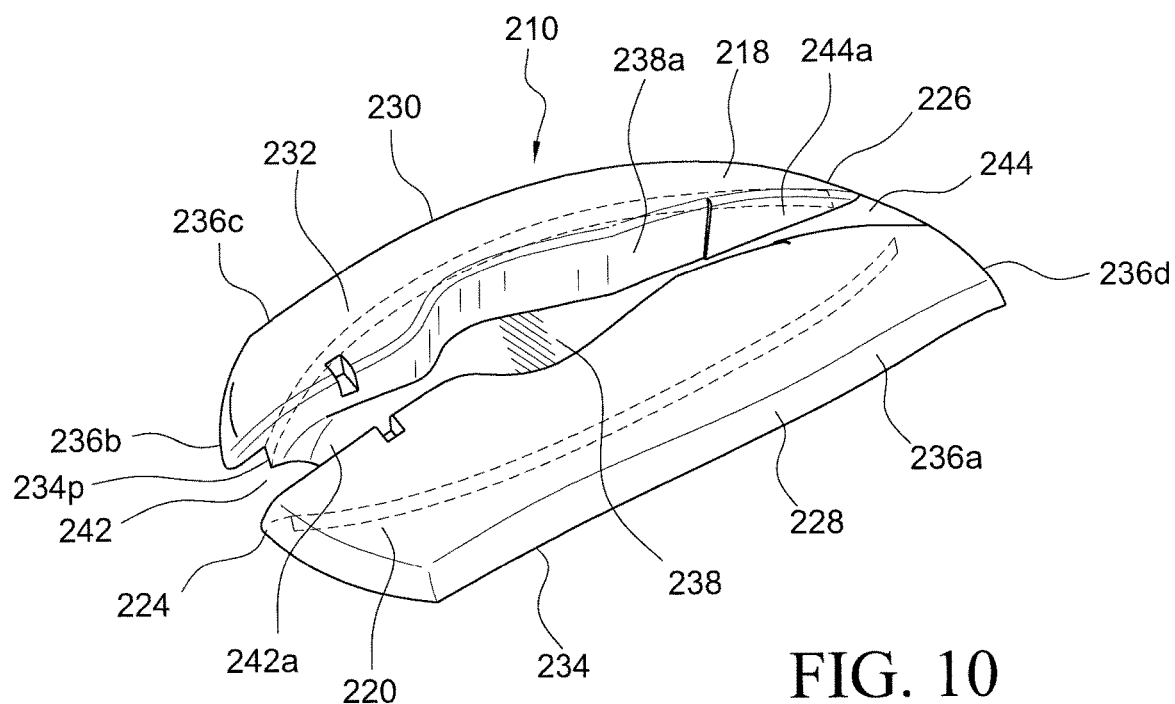
Figure 11:
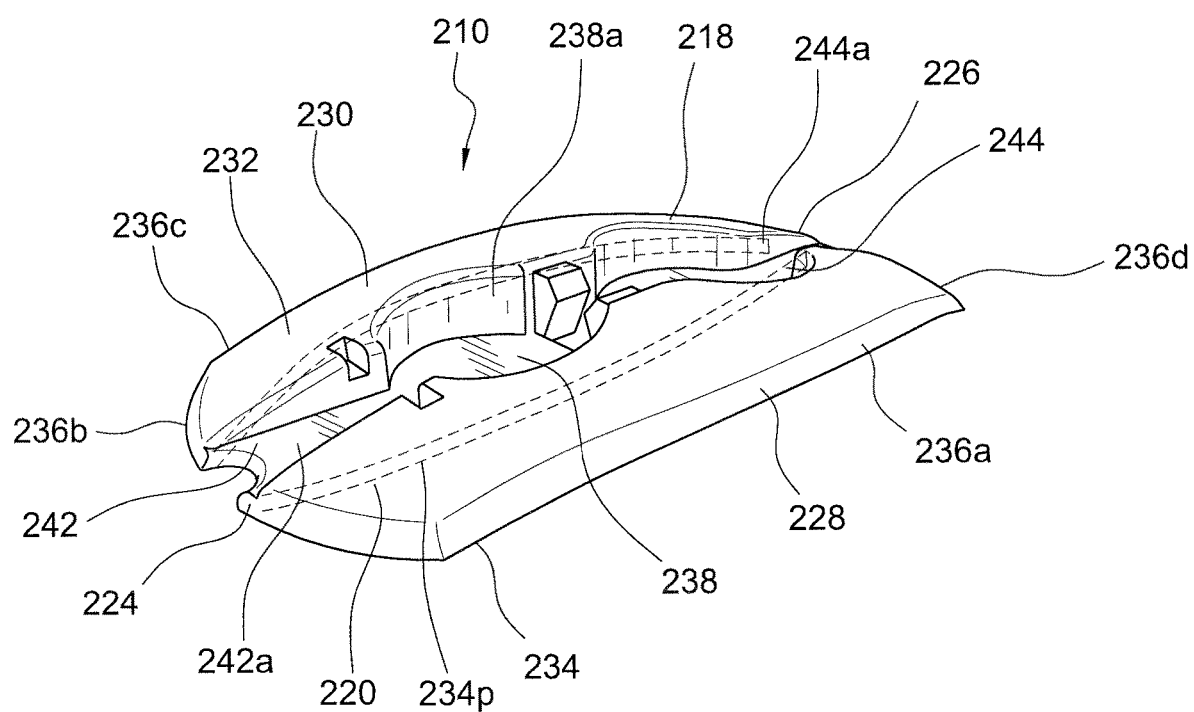
Figure 12:
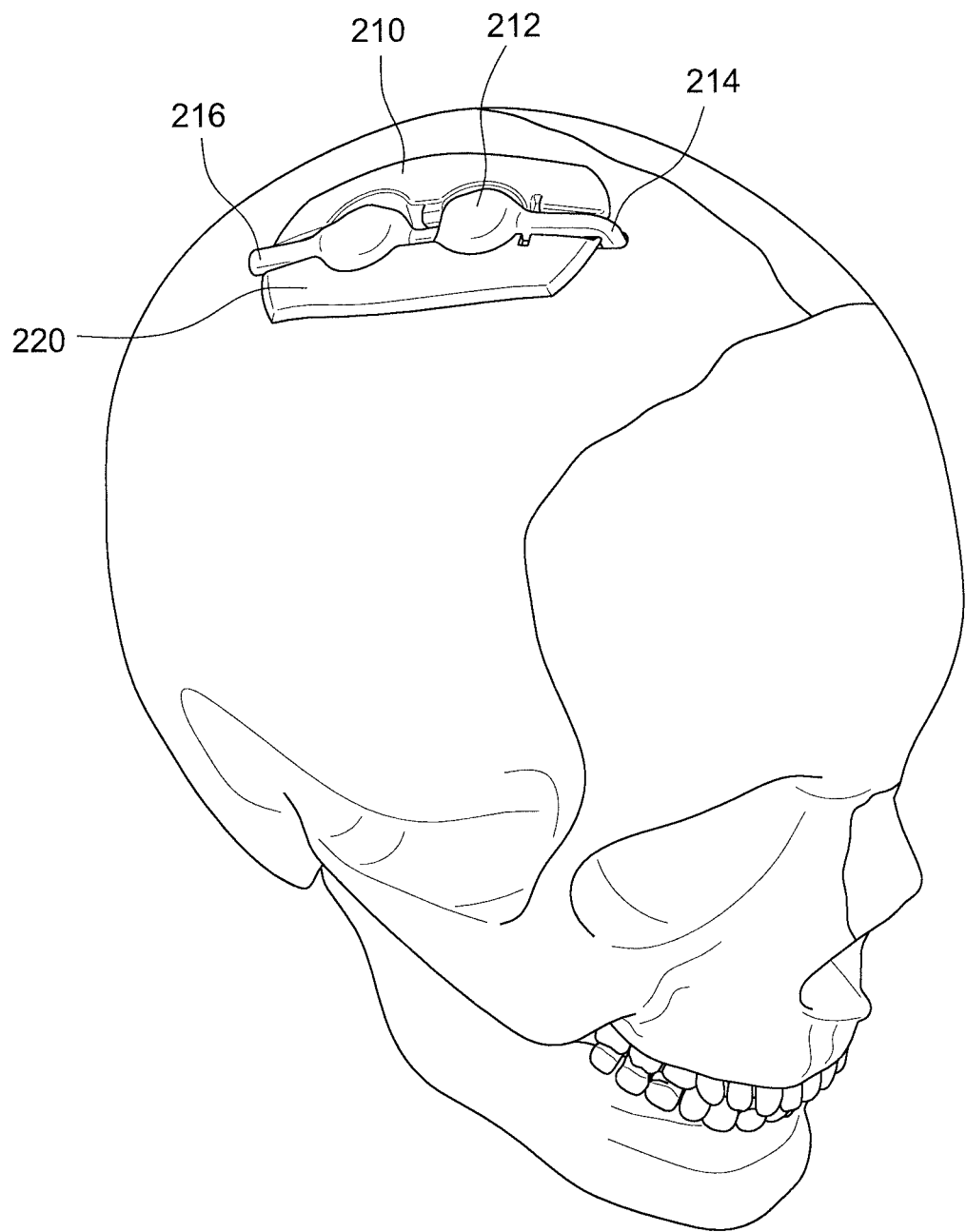
FIG. 12 is a perspective view of a cerebral spinal fluid shunt plug in accordance with the embodiment shown with reference to FIGS. 9, 10, and 11.
Figure 13:
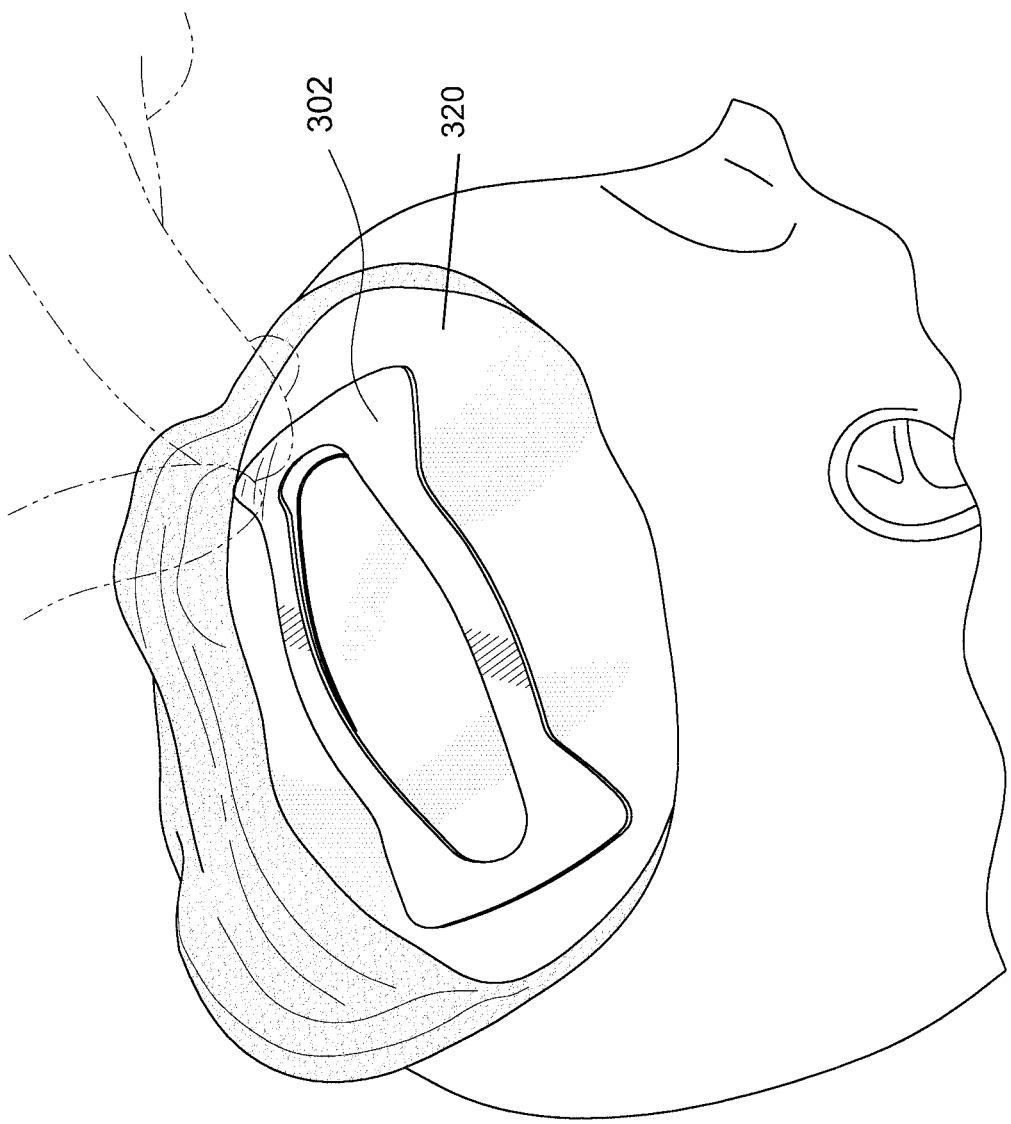
FIGS. 13-18 show the steps associated with the implantation of a cerebral spinal fluid shunt plug in accordance with the embodiment disclosed with reference to FIGS. 9, 10, and 11.
Figure 14:
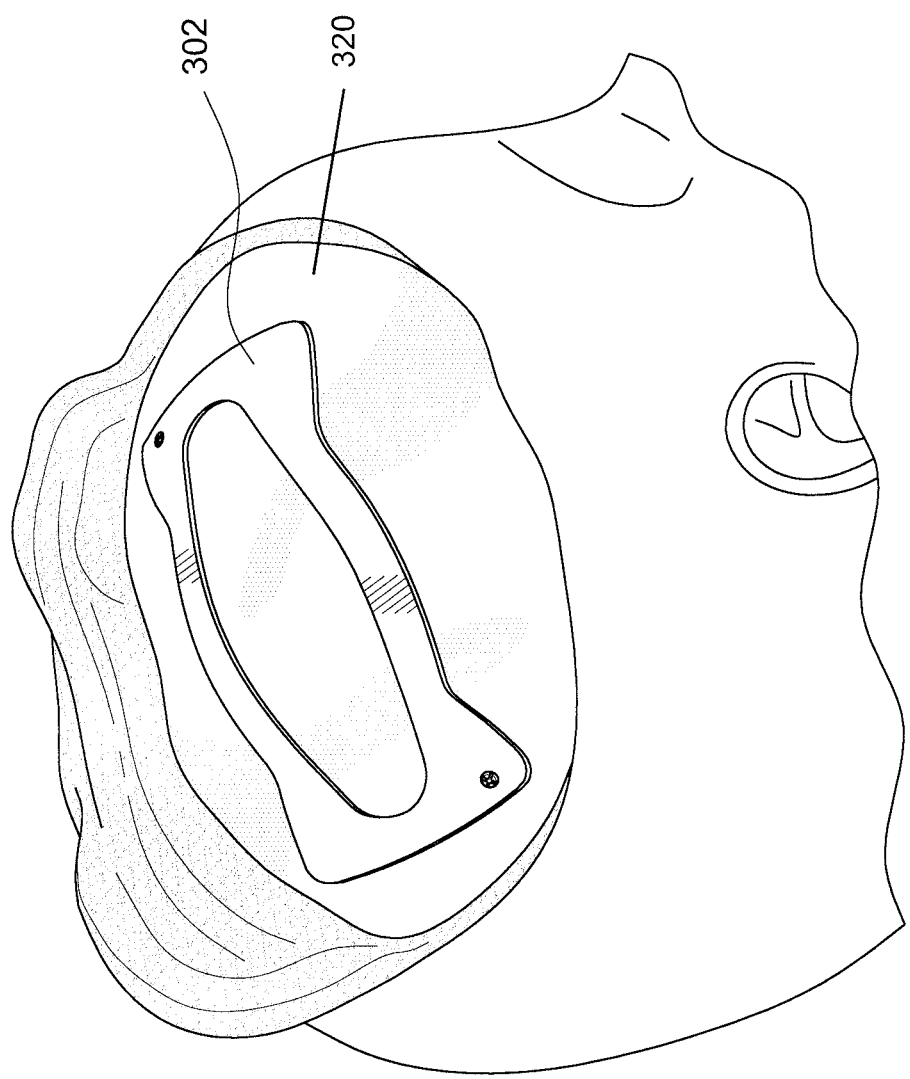

As discussed above, the shunt plug of the present invention may take various shapes. One possible shape where simplicity is considered to be important might involve an elliptically shaped shunt plug housing 18 as shown with reference to FIG. 8. Such an embodiment would require a cranial hole 100 formed by the creation of two burr holes 101 with two connecting cuts 103 made in the shape of the shunt plug 10 so as to allow for placement of the shunt plug 10 within the cranial hole 100. It is, however, appreciated the cranial hole may be made using any method of creating an elliptical craniectomy acceptable by those skilled in the art. When using such an embodiment, it is appreciated variations in the cuts 103 between the two burr holes 101 are likely and the shunt plug 10 is therefore provided with a plurality of attachment tabs 95 that may be used to secure the shunt plug 10 to the area of the skull 120 immediately adjacent to the cranial hole 100.

Referring to FIGS. 13 to 18, and with particular reference to the embodiment disclosed in FIGS. 9 to 18, the procedure is first initiated by making the required incision for passage of the peritoneal catheter 216. Thereafter, a cranial incision is made and the cranial hole 300 in the skull 320 is created utilizing a template 302 (shown in broken lines). In accordance with a preferred embodiment, and considering the elliptical shape of the cranial hole 300, burr holes are formed at the respective ends of the template 302, and the remainder of the skull 320 is cut away along the lines as defined by the template 302. As with the prior embodiment, it is appreciated the cranial hole may be made using any method of creating an elliptical craniectomy acceptable by those skilled in the art. Given the matching shape of the cranial hole 300 and the shunt plug 210, the shunt plug 210 will fit snugly within the cranial hole 300 thereby minimizing potential movement after completion of the procedure.

With the cranial hole 300 completed, the ventricular catheter 214 is positioned within the ventricle and the peritoneal catheter 216 is positioned with the body as using well know medical procedures. Thereafter, the shunt plug housing 218 is positioned within the cranial hole 300 with the upper surface 232 facing upwardly, and the ventricular catheter 214 is cut to an appropriate length. The ends of the peritoneal catheter 216 and the ventricular catheter 214 adjacent the shunt plug 210 are then secured to the shunt valve 212 and the shunt valve 212 is positioned within the shunt plug housing 218. In particular, the shunt plug 210 is mounted within the cranial hole 300 such that the upper surface 232 is substantially flush with the outer surface of the skull 320 and the projection 234p along the lower surface 234 is positioned within the cranial hole 300. As such, portions along the periphery of the shunt plug housing 218 overlie the skull 320, and screws may be passed therethrough to facilitate secure attachment of the shunt plug 210 to the skull. It is, however, appreciated the exact positioning of the shunt plug will vary based upon specific anatomical characteristics of the patient. Once the shunt plug 210 is properly positioned and secured in place using known techniques, the shunt valve 212 is actuated utilizing well known procedures, and the procedure is completed in accordance with known medical procedures.

With the foregoing in mind, the present shunt plug offers multiple advantages. It eliminates mobility of the shunt valve and/or reservoir. As a result, the shunt valve location is known and will not migrate caudal, cephalad, anterior, or posterior which can cause challenges during revision surgery. The ventricular catheter is a precise distance from the shunt valve to the ventricle, therefore mobility of the shunt valve can displace the location of the ventricular catheter. The present shunt plug eliminates cranial deformity as it avoids the need to implant the shunt valve on top of the cranium and underneath the scalp. As a result, pressure on the scalp is minimized along with any accompanying complications such as pain or implant extrusion. In addition, the present shunt plug minimizes micro-motion; that is, the well documented fact that implant micro-motion can lead to bone resorption (causing further deformity) and can lead to infection. Finally, the present shunt plug minimizes catheter kinking as the sharpest angle in the catheters pathway is the top of the perforator made burr hole and by controlling the angle of entry of the catheter the risk of occlusion is minimized.

It is appreciated that once the cerebral spinal fluid shunt plug of the present invention is implanted within the cranium and covered by the scalp, it may be desirable to identify, for example, via triangulation, a specific point or points on the cerebral spinal fluid shunt plug, in particular, the shunt valve itself; for example, to identify and/or locate the center of the programmable portion of the programmable shunt valve or reservoir. In order to achieve this, and with reference to FIGS. 19 to 22, various embodiments are disclosed. It is appreciated these variations are disclosed in accordance with the embodiment described with reference to FIGS. 11 and 12, and the variations described herein may be applied to any of the embodiments disclosed herein.

Figure 19:
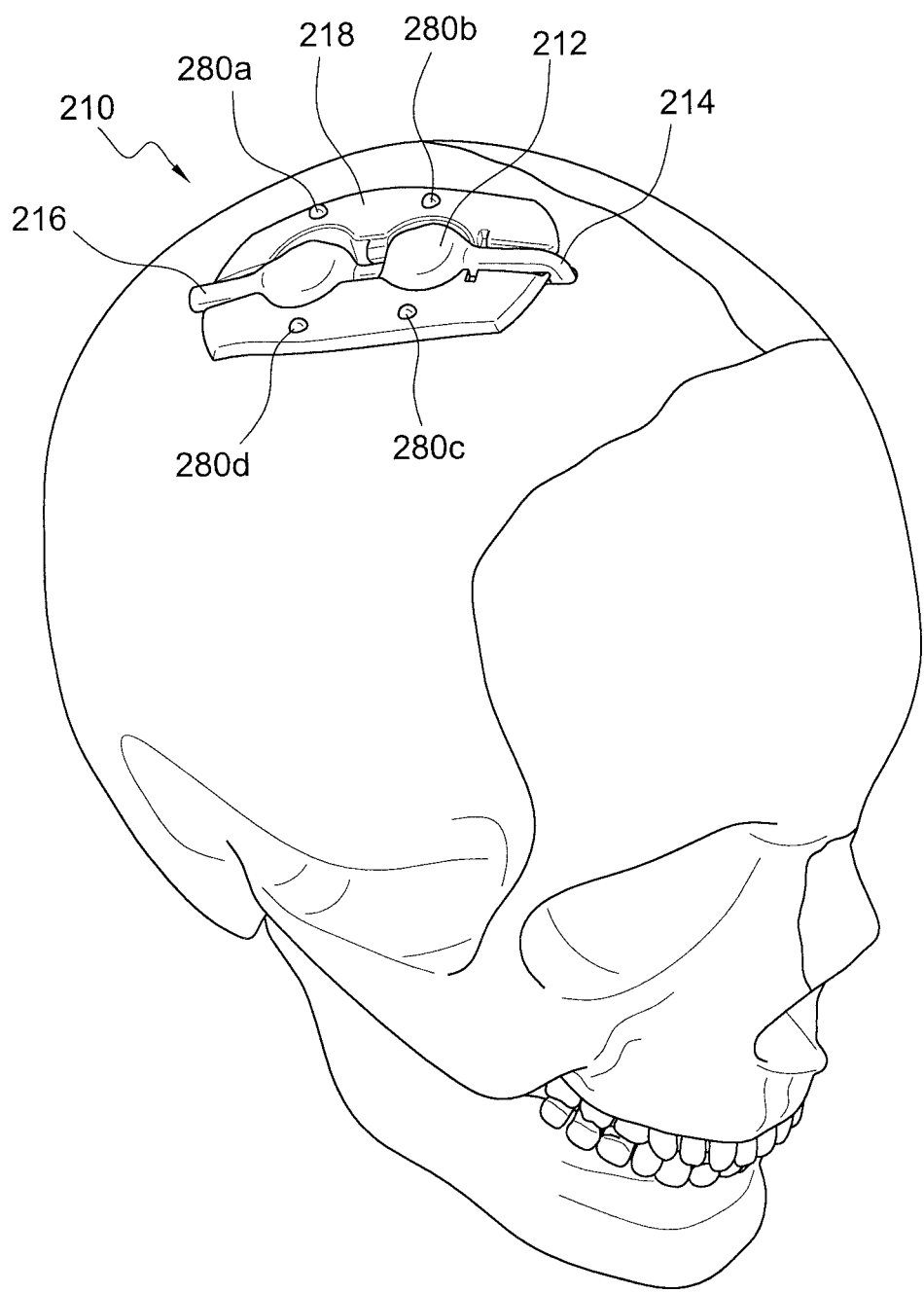
FIGS. 19, 20, 21, and 22 are perspective views of alternate embodiments of a shunt plug in accordance with the present invention.
Figure 20:
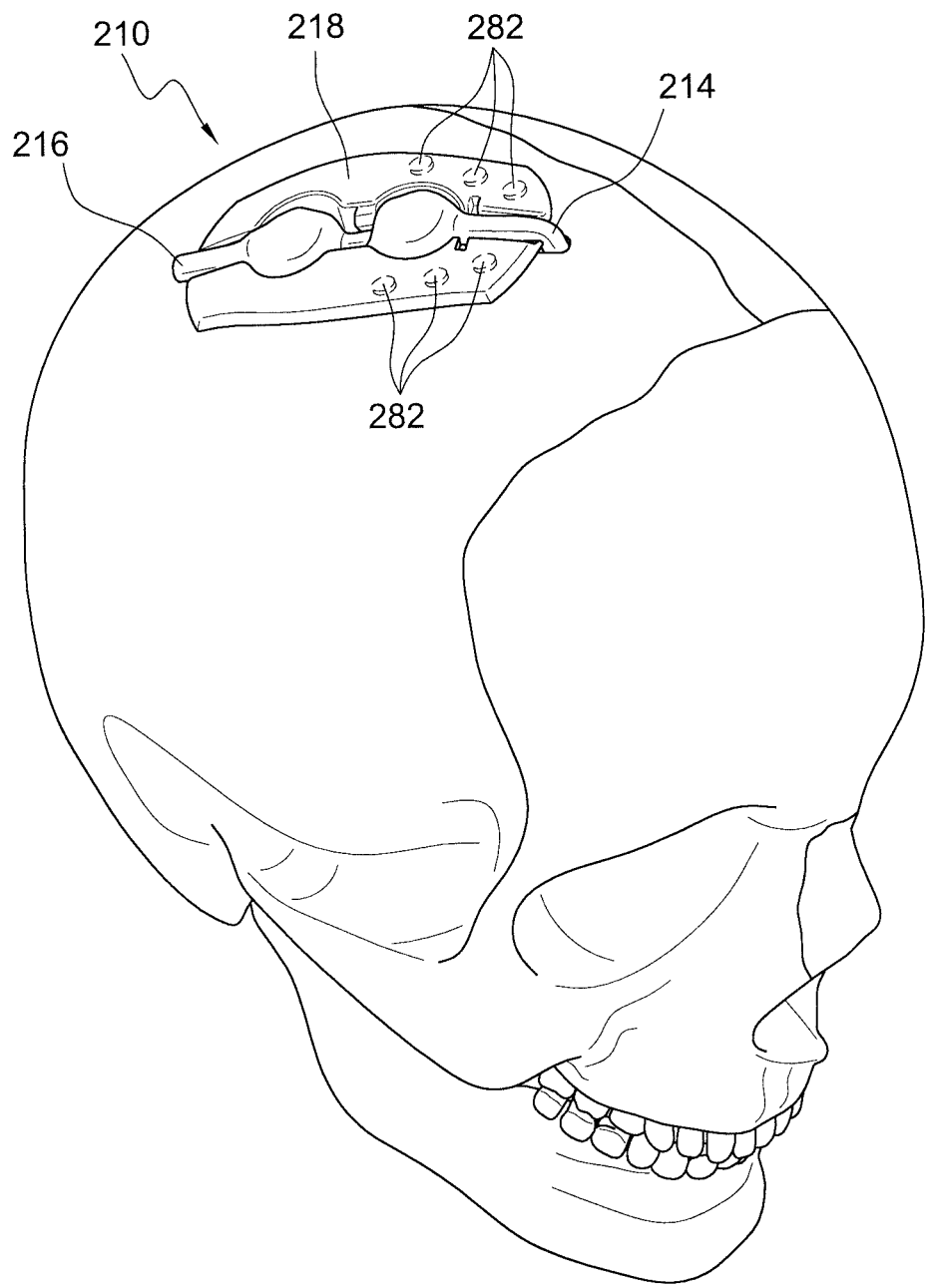
Figure 21:
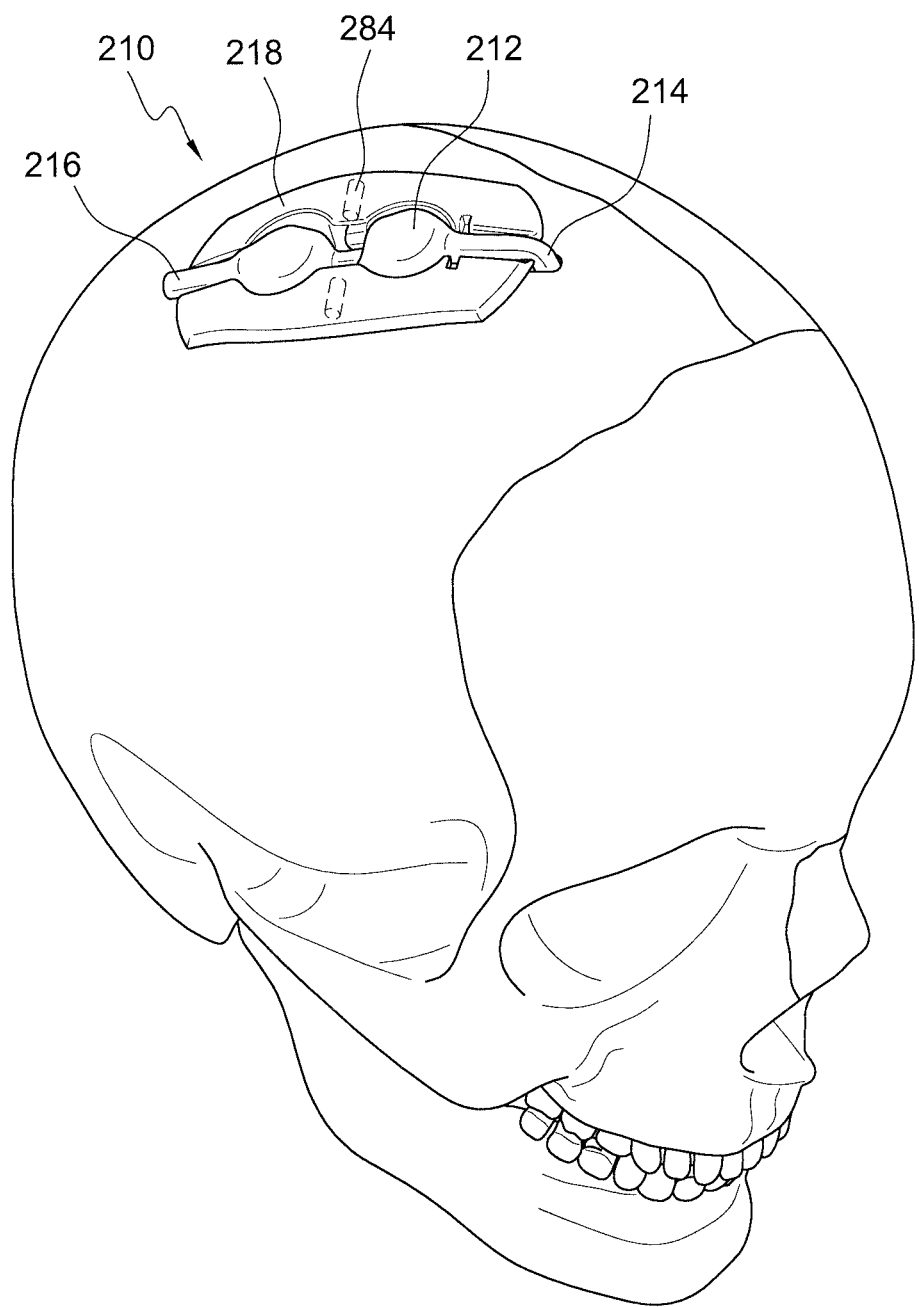
Figure 22:
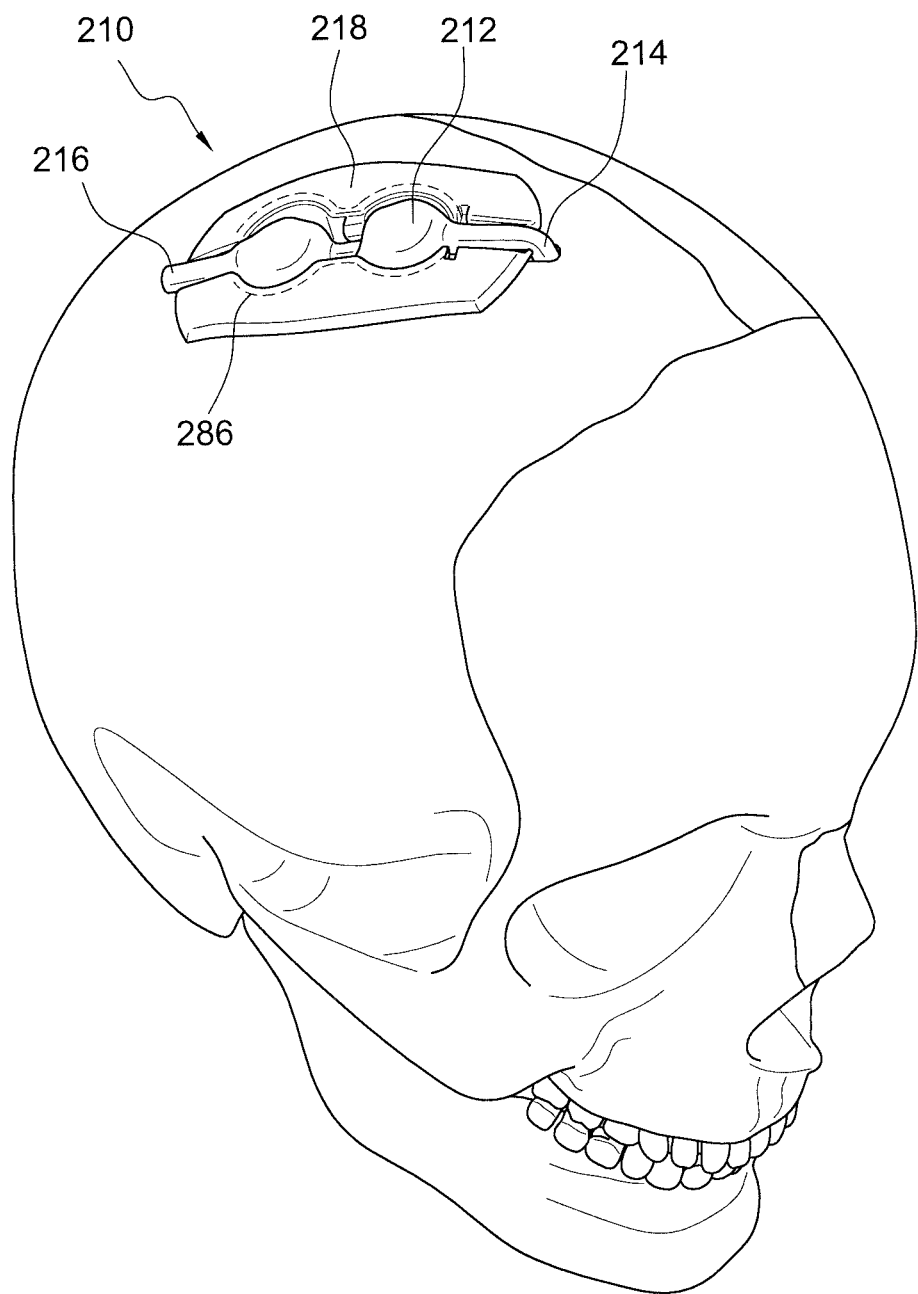

In accordance with the embodiment disclosed with reference to FIG. 19, physical bumps 280*a-d* are provided on the housing 218 of the shunt plug 210. While four bumps are shown in accordance with a disclosed embodiment, it is appreciated the number and location of the bumps may be varied to suit specific needs. In accordance with the embodiment disclosed with reference to FIG. 20, magnets or ferromagnetic properties 282 are integrated into the housing 218. The magnets or ferromagnetic properties 282 are oriented in the housing 218 to allow an external magnet to be employed in triangulating a particular location upon the shunt plug 210. In accordance with the embodiment disclosed with reference to FIG. 21, an RFID (radio-frequency identification) device 284 is embedded in the housing 218 of the shunt plug 210 with the ability to identify a point on the shunt plug 210. In accordance with the embodiment disclosed with reference to FIG. 22, radiographic and/or acoustic properties 286 are integrated into the housing 218 that allow specific points of the shunt plug 210 to be seen by imaging modalities (CT, MRI, X-ray, Ultrasound, etc. . . . ). While the various identification devices described above are integrated into the housing, it is appreciated they might also be integrated into the shunt valve without departing from the spirit of the present invention.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A cerebral spinal fluid assembly including a housing in which a shunt valve is positioned, comprising:

the housing including an upper surface, a lower surface, side walls extending between the upper surface and the lower surface, a shunt valve receiving recess formed in the upper surface, a first access hole or passageway defined by a recessed surface along the upper surface of the housing, and a second access hole or passageway defined by a recessed surface along the upper surface of the housing, the first and second access holes or passageways extend from an exterior surface of the housing to the shunt valve receiving recess allowing the shunt valve receiving recess to communicate with an exterior of the housing, the housing being shaped and dimensioned for positioning a substantial portion thereof within a physician formed cranial hole, the first access hole or passageway and the second access hole or passageway being shaped and dimensioned to receive a ventricular catheter and a peritoneal catheter through the first access hole or passageway and the second access hole or passageway, respectively, for direct connection with the shunt valve received within the shunt valve receiving recess of the housing thereby permitting the shunt valve positioned in the shunt valve receiving recess to communicate with the exterior of the housing through the ventricular catheter and the peritoneal catheter received in the first access hole or passageway and the second access hole or passageway, respectively; and the shunt valve, separate and distinct from the housing, shaped and dimensioned for selective positioning within the shunt valve receiving recess of the housing, the shunt valve shaped and dimensioned to avow direct connection to the ventricular catheter and the peritoneal catheter with the ventricular catheter and peritoneal catheter passing through the first access hole or passageway and the second access hole or passageway for direct connection with the shunt valve.

2. The assembly according to claim 1, wherein the housing includes a bottom first housing member.

3. The assembly according to claim 2, wherein the housing includes a top second housing member, wherein the bottom first housing member and top second housing member are shaped and dimensioned for mating so as to define the housing in which the shunt valve is positioned.

4. The assembly according to claim 3, wherein the shunt valve receiving recess is defined by recessed surfaces formed along surfaces of the bottom first housing member and the top second housing member.

5. The assembly according to claim 1, wherein the housing lower surface includes a projection configured to fit within the cranial hole to assist in holding the housing in position.

6. The assembly according to claim 5, wherein the projection is elliptically shaped to fit in a cranial hole.

7. The assembly according to claim 1, further including bumps used in identifying a specific point or points on the housing.

8. The assembly according to claim 1, further including magnets or ferromagnetic properties used in identifying a specific point or points on the housing.

9. The assembly according to claim 1, further including an RFID (radio-frequency identification) device used in identifying a specific point or points on the housing.

10. The assembly according to claim 1, further including radiographic and/or acoustic properties used in identifying a specific point or points on the housing.

11. The assembly according to claim 1, wherein portions along a periphery of the housing are configured to overlay the skull and receive screws to fasten the housing to the skull.

12. The assembly according to claim 1, wherein the first access hole or passageway extends from the shunt valve receiving recess to a side wall of the housing and the second access hole or passageway extends from the shunt valve receiving recess to a side wall of the housing.

13. The assembly according to claim 1, wherein the housing consists essentially of a first housing member including a upper surface, a lower surface, side walls extending between the upper surface and the lower surface, a recess formed in the upper surface a first access hole or passageway defined by a recessed surface in the upper surface, and a second access hole or passageway defined by a recessed surface in the upper surface such that when the shunt valve is positioned within the recess of the housing the shunt valve is uncovered.

14. The assembly according to claim 1, further including the ventricular catheter directly connected to the shunt valve and positioned within the first access hole or passageway and the peritoneal catheter directly connected to the shunt valve and positioned within the second access hole or passageway.

15. A cerebral spinal fluid assembly including a housing in which a shunt valve is positioned, comprising:

the housing including a bottom first housing member and a top second housing member, wherein the bottom first housing member and top second housing member are shaped and dimensioned for mating at a junction of the first housing member and the second housing member so as to define the housing with a shunt valve receiving recess formed between the bottom first housing member and the top second housing member, the housing further including first and second access holes or passageways extending from an exterior surface of the housing to the shunt valve receiving recess allowing the recess to communicate with an exterior of the housing, the first and second access holes or passageways being defined by recessed surfaces formed along the bottom first housing member and/or the top second housing member, the housing being shaped and dimensioned for positioning a substantial portion of the housing within a physician formed cranial hole such that an upper surface of the housing is flush with a surface of a skull, the first access hole or passageway and the second access hole or passageway being shaped and dimensioned to receive a ventricular catheter and a peritoneal catheter to pass therethrough for direct connection with the shunt valve; and the shunt valve, separate and distinct from the housing, shaped and dimensioned for selective positioning within the shunt valve receiving recess of the housing, the shunt valve being shaped and dimensioned to avow direct connection to the ventricular catheter and the peritoneal catheter with the ventricular catheter and peritoneal catheter passing fully through the first access hole or passageway and the second access hole or passageway for direct connection for direct connection with the shunt valve received within the shunt valve receiving recess of the housing thereby permitting the shunt valve positioned in the shunt valve receiving recess to communicate with the exterior of the housing through the ventricular catheter and the peritoneal catheter received in the first access hole or passageway and the second access hole or passageway, respectively.

* * * * *